United States Patent
Kural

(10) Patent No.: US 11,447,828 B2
(45) Date of Patent: *Sep. 20, 2022

(54) METHODS AND SYSTEMS FOR DETECTING SEQUENCE VARIANTS

(71) Applicant: Seven Bridges Genomics Inc., Cambridge, MA (US)

(72) Inventor: Deniz Kural, Cambridge, MA (US)

(73) Assignee: Seven Bridges Genomics Inc., Charlestown, MA (US)

( * ) Notice: Subject to any disclaimer, the term of this patent is extended or adjusted under 35 U.S.C. 154(b) by 848 days.

This patent is subject to a terminal disclaimer.

(21) Appl. No.: 16/106,996

(22) Filed: Aug. 21, 2018

(65) Prior Publication Data

US 2019/0169695 A1 Jun. 6, 2019

Related U.S. Application Data

(63) Continuation of application No. 14/517,451, filed on Oct. 17, 2014, now Pat. No. 10,053,736.

(60) Provisional application No. 61/892,670, filed on Oct. 18, 2013.

(51) Int. Cl.
| | | |
|---|---|---|
| *G16B 20/20* | (2019.01) | |
| *G16B 20/00* | (2019.01) | |
| *G16B 30/10* | (2019.01) | |
| *C12Q 1/6886* | (2018.01) | |
| *C12Q 1/6883* | (2018.01) | |

(52) U.S. Cl.
CPC ......... *C12Q 1/6886* (2013.01); *C12Q 1/6883* (2013.01); *G16B 20/00* (2019.02); *G16B 20/20* (2019.02); *G16B 30/10* (2019.02); *C12Q 2600/112* (2013.01); *C12Q 2600/156* (2013.01); *C12Q 2600/16* (2013.01)

(58) Field of Classification Search
CPC ........ G06N 20/00; G06N 7/005; G06N 5/022; G06N 5/04; G06N 3/08; G06N 3/084; G06N 20/10; G06N 3/063; G06N 5/025; G06N 5/046; G06N 5/02; G06N 5/003; G06N 3/0472; G06N 3/02; G06N 7/00; G06N 3/0427; G06N 3/0481; G06N 3/082; G06N 7/023; G06N 5/047; G06N 3/00; G06N 5/00; G16B 20/00; G16B 30/00; G16B 40/00; G16B 20/20; G16B 30/10; G16B 5/00; G16B 50/00; G16B 40/20; G16B 30/20; G16B 25/00; G16B 5/20; G16B 25/10; G16B 40/30; G16B 45/00; G16B 50/30; G16B 50/10; G16B 40/10; G16B 20/30; G16B 20/40; G16B 5/10; G16B 35/00; G16B 20/10; G16B 99/00; G16B 15/00; G16B 20/50; G16B 50/20; G16H 50/20; G16H 50/30; G16H 50/70; G16H 10/60; G16H 50/50; G16H 70/60; G16H 10/20; G16H 70/20; G16H 15/00; G16H 10/40; G16H 70/00; G16H 50/00; G16H 50/80; G16H 80/00; G16H 10/00; G06F 16/9024; G06F 40/30; G06F 16/285; G06F 9/5072; G06F 16/245; G06F 16/248; G06F 16/9535; G06F 40/205; G06F 16/90335; G06F 17/18; G06F 16/20; G06F 16/24534; G06F 9/5066; G06F 8/34; G06F 16/24578; G06F 16/367; G06F 16/144; G06F 16/435; G06F 16/284; G06F 16/23; G06F 16/244; G06F 16/8373; G06F 16/9577; G06F 16/904; G06F 16/24564; G06F 2111/10; G06F 16/00; G06F 40/216; G06F 16/538; G06F 16/90344; G06F 16/907; G06K 9/6269; G06K 9/6215; G06K 9/6296; G06K 9/4628; G06K 9/6217; G06K 9/6267; G06K 9/6256; G06K 2209/07; G06K 2209/09; G06K 9/6255; G06K 9/6298; G06K 9/6814; G06K 9/4638; G06K 9/6201; G06K 9/627; G06K 9/6221;
(Continued)

(56) References Cited

U.S. PATENT DOCUMENTS

| | | |
|---|---|---|
| 4,683,195 A | 7/1987 | Mullis et al. |
| 4,683,202 A | 7/1987 | Mullis |

(Continued)

FOREIGN PATENT DOCUMENTS

| | | |
|---|---|---|
| EP | 3058093 B1 | 7/2019 |
| KR | 101282798 B1 | 7/2013 |

(Continued)

OTHER PUBLICATIONS

Herold (2012) Tumor progression modelling without likelihoods. In: Kestler et al. (eds) Statistical computing 2012—abstracts der 44. Arbeitstagung, UULM, UIB, Jun. 24-Jun. 27, 2012. (Year: 2012).*
Agarwal, 2013, SINNET: Social Interaction Network Extractor from Text, Proc IJCNLP 33-36.

(Continued)

*Primary Examiner* — Mary K Zeman
(74) *Attorney, Agent, or Firm* — Wolf, Greenfield & Sacks, P.C.

(57) ABSTRACT

The invention includes methods and systems for identifying diseased-induced mutations by producing multi-dimensional reference sequence constructs that account for variations between individuals, different diseases, and different stages of those diseases. Once constructed, these reference sequence constructs can be used to align sequence reads corresponding to genetic samples from patients suspected of having a disease, or who have had the disease and are in suspected remission. The reference sequence constructs also provide insight to the genetic progression of the disease.

20 Claims, 12 Drawing Sheets

Specification includes a Sequence Listing.

(58) Field of Classification Search
CPC .. G06K 9/6224; G06K 9/6277; G06K 9/6293; G06K 9/00617; G06K 9/52; G06K 9/6272
See application file for complete search history.

(56) References Cited

U.S. PATENT DOCUMENTS

| | | |
|---|---|---|
| 4,988,617 A | 1/1991 | Landegren et al. |
| 5,234,809 A | 8/1993 | Boom et al. |
| 5,242,794 A | 9/1993 | Whiteley et al. |
| 5,494,810 A | 2/1996 | Barany et al. |
| 5,511,158 A | 4/1996 | Sims |
| 5,583,024 A | 12/1996 | McElroy et al. |
| 5,674,713 A | 10/1997 | McElroy et al. |
| 5,700,673 A | 12/1997 | McElroy et al. |
| 5,701,256 A | 12/1997 | Marr et al. |
| 6,054,278 A | 4/2000 | Dodge et al. |
| 6,210,891 B1 | 4/2001 | Nyren et al. |
| 6,223,128 B1 | 4/2001 | Allex et al. |
| 6,306,597 B1 | 10/2001 | Macevicz |
| 6,582,938 B1 | 6/2003 | Su et al. |
| 6,818,395 B1 | 11/2004 | Quake et al. |
| 6,828,100 B1 | 12/2004 | Ronaghi |
| 6,833,246 B2 | 12/2004 | Balasubramanian |
| 6,890,763 B2 | 5/2005 | Jackowski et al. |
| 6,911,345 B2 | 6/2005 | Quake et al. |
| 6,925,389 B2 | 8/2005 | Hitt et al. |
| 6,989,100 B2 | 1/2006 | Norton |
| 7,169,560 B2 | 1/2007 | Lapidus et al. |
| 7,232,656 B2 | 6/2007 | Balasubramanian et al. |
| 7,282,337 B1 | 10/2007 | Harris |
| 7,321,623 B2 | 1/2008 | Dambrackas |
| 7,483,585 B2 | 1/2009 | Brakus, Jr. |
| 7,577,554 B2 | 8/2009 | Lystad et al. |
| 7,580,918 B2 | 8/2009 | Chang et al. |
| 7,598,035 B2 | 10/2009 | Macevicz |
| 7,620,800 B2 | 11/2009 | Huppenthal et al. |
| 7,776,616 B2 | 8/2010 | Heath et al. |
| 7,809,509 B2 | 10/2010 | Milosavljevic |
| 7,835,871 B2 | 11/2010 | Kain et al. |
| 7,885,840 B2 | 2/2011 | Sadiq et al. |
| 7,917,302 B2 | 3/2011 | Rognes |
| 7,957,913 B2 | 6/2011 | Chinitz et al. |
| 7,960,120 B2 | 6/2011 | Rigatti et al. |
| 8,146,099 B2 | 3/2012 | Tkatch et al. |
| 8,165,821 B2 | 4/2012 | Zhang |
| 8,209,130 B1 | 6/2012 | Kennedy et al. |
| 8,340,914 B2 | 12/2012 | Gatewood et al. |
| 8,370,079 B2 | 2/2013 | Sorenson et al. |
| 8,639,847 B2 | 1/2014 | Blaszczak et al. |
| 8,972,201 B2 | 3/2015 | Mande et al. |
| 9,063,914 B2 | 6/2015 | Kural et al. |
| 9,092,402 B2 | 7/2015 | Kural et al. |
| 9,116,866 B2 | 8/2015 | Kural |
| 9,390,226 B2 | 7/2016 | Kural |
| 9,817,944 B2 | 11/2017 | Kural |
| 10,053,736 B2 * | 8/2018 | Kural ................... G16B 20/00 |
| 10,364,468 B2 | 7/2019 | Lee et al. |
| 2002/0164629 A1 | 11/2002 | Quake et al. |
| 2002/0190663 A1 | 12/2002 | Rasmussen |
| 2004/0023209 A1 | 2/2004 | Jonasson |
| 2005/0089906 A1 | 4/2005 | Furuta et al. |
| 2006/0024681 A1 | 2/2006 | Smith et al. |
| 2006/0195269 A1 | 8/2006 | Yeatman et al. |
| 2006/0292611 A1 | 12/2006 | Berka et al. |
| 2007/0114362 A1 | 5/2007 | Feng et al. |
| 2007/0166707 A1 | 7/2007 | Schadt et al. |
| 2008/0003571 A1 | 1/2008 | McKernan et al. |
| 2008/0077607 A1 | 3/2008 | Gatewood et al. |
| 2008/0251711 A1 | 10/2008 | Reilly |
| 2008/0281463 A1 | 11/2008 | Suh et al. |
| 2008/0294403 A1 | 11/2008 | Zhu et al. |
| 2009/0026082 A1 | 1/2009 | Rothberg et al. |
| 2009/0119313 A1 | 5/2009 | Pearce |
| 2009/0127589 A1 | 5/2009 | Rothberg et al. |
| 2009/0164135 A1 | 6/2009 | Brodzik et al. |
| 2009/0191565 A1 | 7/2009 | Lapidus et al. |
| 2009/0233809 A1 | 9/2009 | Faham et al. |
| 2009/0300781 A1 | 12/2009 | Bancroft et al. |
| 2009/0318310 A1 | 12/2009 | Liu et al. |
| 2009/0325145 A1 | 12/2009 | Sablon et al. |
| 2010/0010992 A1 | 1/2010 | Morris |
| 2010/0035252 A1 | 2/2010 | Rothberg et al. |
| 2010/0041048 A1 | 2/2010 | Diehl et al. |
| 2010/0137143 A1 | 6/2010 | Rothberg et al. |
| 2010/0169026 A1 | 7/2010 | Sorenson et al. |
| 2010/0188073 A1 | 7/2010 | Rothberg et al. |
| 2010/0197507 A1 | 8/2010 | Rothberg et al. |
| 2010/0240046 A1 | 9/2010 | Palmer et al. |
| 2010/0282617 A1 | 11/2010 | Rothberg et al. |
| 2010/0285578 A1 | 11/2010 | Selden et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0004413 A1 | 1/2011 | Carnevali et al. |
| 2011/0009278 A1 | 1/2011 | Kain et al. |
| 2011/0098193 A1 | 4/2011 | Kingsmore et al. |
| 2011/0207135 A1 | 8/2011 | Faham et al. |
| 2011/0257889 A1 | 10/2011 | Klammer et al. |
| 2012/0030566 A1 | 2/2012 | Victor |
| 2012/0040851 A1 | 2/2012 | Lieberman et al. |
| 2012/0041727 A1 | 2/2012 | Mishra et al. |
| 2012/0045771 A1 | 2/2012 | Beier et al. |
| 2012/0157322 A1 | 6/2012 | Myllykangas et al. |
| 2012/0239706 A1 | 9/2012 | Steinfadt |
| 2012/0330566 A1 | 12/2012 | Chaisson |
| 2013/0029879 A1 | 1/2013 | Shetty et al. |
| 2013/0035904 A1 | 2/2013 | Kuhn |
| 2013/0059738 A1 | 3/2013 | Leamon et al. |
| 2013/0059740 A1 | 3/2013 | Drmanac et al. |
| 2013/0073214 A1 | 3/2013 | Hyland et al. |
| 2013/0124100 A1 | 5/2013 | Drmanac et al. |
| 2013/0232480 A1 | 9/2013 | Winterfeldt et al. |
| 2013/0289099 A1 | 10/2013 | Le Goff et al. |
| 2013/0311106 A1 | 11/2013 | White et al. |
| 2013/0332081 A1 | 12/2013 | Reese et al. |
| 2013/0345066 A1 | 12/2013 | Brinza et al. |
| 2014/0012866 A1 | 1/2014 | Bowman et al. |
| 2014/0025312 A1 | 1/2014 | Chin et al. |
| 2014/0051588 A9 | 2/2014 | Drmanac et al. |
| 2014/0066317 A1 | 3/2014 | Talasaz |
| 2014/0129201 A1 | 5/2014 | Kennedy et al. |
| 2014/0136120 A1 | 5/2014 | Colwell et al. |
| 2014/0200147 A1 | 7/2014 | Bartha et al. |
| 2014/0278590 A1 | 9/2014 | Abbassi et al. |
| 2014/0280360 A1 | 9/2014 | Webber et al. |
| 2014/0281708 A1 | 9/2014 | Adam et al. |
| 2014/0323320 A1 | 10/2014 | Jia et al. |
| 2015/0020061 A1 | 1/2015 | Ravi |
| 2015/0056613 A1 | 2/2015 | Kural |
| 2015/0057946 A1 | 2/2015 | Kural |
| 2015/0066383 A1 | 3/2015 | Wernicke |
| 2015/0094212 A1 | 4/2015 | Gottimukkala et al. |
| 2015/0110754 A1 | 4/2015 | Bai et al. |
| 2015/0112602 A1 | 4/2015 | Kural et al. |
| 2015/0112658 A1 | 4/2015 | Kural et al. |
| 2015/0197815 A1 | 7/2015 | Kural |
| 2015/0199472 A1 | 7/2015 | Kural |
| 2015/0199473 A1 | 7/2015 | Kural |
| 2015/0199474 A1 | 7/2015 | Kural |
| 2015/0199475 A1 | 7/2015 | Kural |
| 2015/0227685 A1 | 8/2015 | Kural |
| 2015/0293994 A1 | 10/2015 | Kelly |
| 2015/0302145 A1 | 10/2015 | Kural et al. |
| 2015/0310167 A1 | 10/2015 | Kural et al. |
| 2015/0344970 A1 | 12/2015 | Vogelstein et al. |
| 2015/0347678 A1 | 12/2015 | Kural |
| 2015/0356147 A1 | 12/2015 | Mishra et al. |
| 2016/0259880 A1 | 9/2016 | Semenyuk |
| 2016/0306921 A1 | 10/2016 | Kural |
| 2016/0364523 A1 | 12/2016 | Locke et al. |
| 2017/0058320 A1 | 3/2017 | Locke et al. |
| 2017/0058341 A1 | 3/2017 | Locke et al. |

(56) References Cited

U.S. PATENT DOCUMENTS

| | | | |
|---|---|---|---|
| 2017/0058365 | A1 | 3/2017 | Locke et al. |
| 2017/0193351 | A1 | 7/2017 | Noyes et al. |
| 2017/0198351 | A1 | 7/2017 | Lee et al. |
| 2017/0199959 | A1 | 7/2017 | Locke |
| 2017/0199960 | A1 | 7/2017 | Ghose et al. |
| 2017/0242958 | A1 | 8/2017 | Brown |
| 2020/0165683 | A1 | 5/2020 | Lee et al. |

FOREIGN PATENT DOCUMENTS

| | | | |
|---|---|---|---|
| WO | WO 2007/086935 | A3 | 8/2007 |
| WO | WO 2010/010992 | A1 | 1/2010 |
| WO | WO 2011/103236 | A2 | 8/2011 |
| WO | WO 2011/139797 | A2 | 11/2011 |
| WO | 2012096579 | A3 | 7/2012 |
| WO | 2012098515 | A1 | 7/2012 |
| WO | 2012142531 | A2 | 10/2012 |
| WO | WO 2013/035904 | A1 | 3/2013 |
| WO | WO 2013/043909 | A1 | 3/2013 |
| WO | WO 2013/106737 | A1 | 7/2013 |
| WO | WO 2013/184643 | A1 | 12/2013 |
| WO | 2015027050 | A1 | 2/2015 |
| WO | 2015048753 | A1 | 4/2015 |
| WO | 2015058093 | A1 | 4/2015 |
| WO | 2015058095 | A1 | 4/2015 |
| WO | 2015058097 | A1 | 4/2015 |
| WO | 2015058120 | A1 | 4/2015 |
| WO | 2015061099 | A1 | 4/2015 |
| WO | 2015061103 | A1 | 4/2015 |
| WO | 2015105963 | A1 | 7/2015 |
| WO | 2015123269 | A1 | 8/2015 |
| WO | 2016141294 | A1 | 9/2016 |
| WO | 2016201215 | A1 | 12/2016 |
| WO | 2017066753 | A1 | 4/2017 |
| WO | 2017120128 | A1 | 7/2017 |
| WO | 2017123864 | A1 | 7/2017 |
| WO | 2017147124 | A1 | 8/2017 |

OTHER PUBLICATIONS

Aguiar, 2012, HapCompass: A fast cycle basis algorithm for accurate haplotype assembly of sequence data, J Comp Biol 19(6):577-590.

Aguiar, 2013, Haplotype assembly in polyploid genomes and identical by descent shared tracts, BioInformatics 29(13): i352-i360.

Airoldi, 2008, Mixed membership stochastic blockmodels, JMLR 9:1981-2014.

Albers, 2011, Dindel: Accurate indel calls from short-read data, Genome Research 21:961-973.

Altera, 2007, Implementation of the Smith-Waterman algorithm on reconfigurable supercomputing platform, White Paper ver 1.0 (18 pages).

Altschul, 1986, Optimal Sequence Alignment Using Affine Gap Costs, Bull Math Biol 48(5/6):603-616.

Bansal, 2008, An MCMC algorithm for haplotype assembly from whole-genome sequence data, Genome Res 18:1336-1346.

Bao, 2013, BRANCH: boosting RNA-Seq assemblies with partial or related genomic sequences, Bioninformatics 29 (10):1250-1259.

Barbieri, 2013, Exome sequencing identifies recurrent SPOP, FOXA1 and MED12 mutations in prostate cancer, Nature Genetics 44:6 685-689.

Beerenwinkel, 2007, Conjunctive Bayesian Networks, Bernoulli 13(4), 893-909.

Berlin, 2014, Assembling large genomes with single-molecule sequencing and locality sensitive hashing, bioRxiv preprint (35 pages); retrieved from the internet on Jan. 29, 2015, at.

Bertrand, 2009, Genetic map refinement using a comparative genomic approach, J Comp Biol 16(10):1475-1486.

Black, 2005, A simple answer for a splicing conundrum, PNAS 102:4927-8.

Boyer, 1977, A Fast String Searching Algorithm, Comm ACM 20(10):762-772.

Browning et al, Haplotype phasing: existing methods and new developments, 2011, vol. 12, Nature Reviews Genetics.

Caboche et al, Comparison of mapping algorithms used in high-throughput sequencing: application to Ion Torrent data, 2014, vol. 15, BMC Genomics.

Cartwright, DNA assembly with gaps (DAWG): simulating sequence evolution, 2005, pages iii31-iii38, vol. 21, Oxford University Press.

Chang, 2005, The application of alternative splicing graphs in quantitative analysis of alternative splicing form from EST database, Int J Comp Appl Tech 22(1):14.

Chin, 2013, Nonhybrid finished microbial genome assemblies from long-read SMRT sequencing data, Nat Meth 10 (6):563-569.

Chuang, 2001, Gene recognition based on DAG shortest paths, Bioinformatics 17(Suppl. 1):s56-s64.

Compeau, 2011, How to apply de Bruijn graphs to genome assembly, Nat Biotech 29(11):987-991.

DePristo, 2011, A framework for variation discovery and genotyping using next-generation DNA sequencing data, Nat Gen 43:491-498.

Dinov, 2011, Applications of the pipeline environment for visual informatics and genomic computations, BMC Bioinformatics 12:304.

Duan et al., Optimizing de novo common wheat transcriptome assembly using short-read RNA-Seq data. (2012) pp. 1-12, vol. 13, BMC Genomics.

Dudley, 2009, A quick guide for developing effective bioinformatics programming skills, PLoS Comput Biol 5(12): e1000589.

Durbin, 2014, Efficient haplotype matching and storage using the positional Burrows-Wheeler transform (PBWT), Bioinformatics 30(9):1266-1272.

Endelman, 2011, New algorithm improves fine structure of the barley consensus SNP map, BMC Genomics 12(1):407 (and whole document).

Farrar, 2007, Striped Smith-Waterman speeds database searches six times over other SIMD implementations, Bioinformatics 23(2):156-161.

Fitch, 1970, Distinguishing homologous from analogous proteins, Systematic Zoology 19:99-113.

Flicek, 2009, Sense from sequence reads: methods for alignment and assembly, Nat Meth Suppl 6(11s):s6-s12.

Florea, 2013, Genome-guided transcriptome assembly in the age of next-generation sequencing, IEEE/ACM Trans Comp Biol Bioinf 10(5):1234-1240.

Garber, 2011, Computational methods for transcriptome annotation and quantification using RNA-Seq, Nat Meth 8 (6):469-477.

Gerlinger, 2012, Intratumor Heterogeneity and Branched Evolution Revealed by Multiregion Sequencing, 366:10 883-892.

Gotoh, 1982, An Improved Algorithm for Matching Biological Sequences, J Mol Biol 162:705-708.

Gotoh, 1999, Multiple sequence alignment: algorithms and applications, Adv Biophys 36:159-206.

Grabherr, 2011, Full-length transcriptome assembly from RNA-Seq data without a reference genome, Nat Biotech 29 (7):644-654.

Grasso, 2004, Combining partial order alignment and progressive multiple sequence alignment increases alignment speed and scalability to very large alignment problems, Bioinformatics 20(10):1546-1556.

Guttman, 2010, Ab initio reconstruction of cell type-specific transcriptomes in mouse reveals the conserved multi-exonic structure of lincRNAs, Nat Biotech 28(5):503-510.

Guttman, 2010, Ab initio reconstruction of transcriptomes of pluripotent and lineage committed cells reveals gene structures of thousands of lincRNAs, NIH-PA Author Manuscript.

Haas, 2004, DAGchainer: a tool for mining segmental genome duplications and synteny, Bioinformatics 20 (18):3643-3646.

Harrow, 2012, GENCODE: The reference human genome annotation for The ENCODE Project, Genome Res 22:1760-1774.

He, 2010, Optimal algorithms for haplotype assembly from whole-genome sequence data, Bioinformatics 26:i183-i190.

Heber, 2002, Splicing graphs and EST assembly problems, Bioinformatics 18 Suppl:181-188.

(56) References Cited

OTHER PUBLICATIONS

Hein, 1989, A new method that simultaneously aligns and reconstructs ancestral sequences for any number of homologous sequences when the phylogeny is given, Mol Biol Evol 6(6):649-668.
Hein, 1989, A tree reconstruction method that is economical in the number of pairwise comparisons used, Mol Biol Evol 6(6):649-668.
Homer, 2010, Improved variant discovery through local re-alignment of short-read next generation sequencing data using SRMA, Genome Biol 11 (10):R99.
Horspool, 1980, Practical Fast Searching in Strings, Software—Practice & Experience 10:501-506.
Huang, Chapters: Bio-Sequence Comparison and Alignment, ser. CurrTop Comp Mol Biol. Cambridge, Mass.: The MIT Press, 2002.
Hutchinson, 2014, Allele-specific methylation occurs at genetic variants associated with complex diseases, PLoS One 9(6):e98464.
International Search Report and Written Opinion dated Aug. 31, 2017, for International Application No. PCT/US2017/018830 with International Filing Date Feb. 22, 2017, (11 pages).
International Search Report and Written Opinion dated Mar. 31, 2015 for International Application No. PCT/US2015/010604 filed Jan. 8, 2015 (13 pages).
International Search Report and Written Opinion dated Apr. 19, 2017 for International Patent Application No. PCT/US2017/012015, (14 Pages).
International Search Report and Written Opinion dated Feb. 17, 2015, for International Patent Application No. PCT/US2014/061156, filed Oct. 17, 2014 (19 pages).
International Search Report and Written Opinion dated Jan. 10, 2017, for International Patent Application No. PCT/US16/57324 with International Filing Date Oct. 17, 2016, (7 pages).
International Search Report and Written Opinion dated Mar. 19, 2015, for International Application No. PCT/US2014/061162 with International Filing Date Oct. 17, 2014, (12 pages).
International Search Report and Written Opinion dated May 11, 2015, for International Patent Application No. PCT/US2015/015375 with International Filing Date Feb. 11, 2015, (12 pages).
International Search Report and Written Opinion dated May 5, 2016, for International Patent Application No. PCT/US2016/020899, wiht International Filing Date Mar. 4, 2016, (12 pages).
International Search Report and Written Opinion dated Apr. 7, 2017, for International Patent Application No. PCT/US17/13329, filed Jan. 13, 2017, (9 pages).
International Search Report and Written Opinion dated Dec. 11, 2014, for International Patent Application No. PCT/US14/52065, filed Aug. 21, 2014, (18 pages).
International Search Report and Written Opinion dated on Dec. 30, 2014, for International Patent Application No. PCT/US14/58328, filed Sep. 30, 2014, (22 pages).
International Search Report and Written Opinion dated Feb. 4, 2015, for International Patent Application No. PCT/US2014/061198, filed Oct. 17, 2014, (8 pages).
International Search Report and Written Opinion dated Feb. 10, 2015, for International Patent Application No. PCT/US2014/060690, filed Oct. 15, 2014, (11 pages).
International Search Report and Written Opinion dated Feb. 4, 2015, for Patent Application No. PCT/US2014/061158, filed Oct. 17, 2014, (11 pages).
International Search Report and Written Opinion dated Jan. 27, 2015, for International Patent Application No. PCT/US2014/060680, filed Oct. 215, 2014, (11 pages).
International Search Report and Written Opinion dated Sep. 2, 2016, for International Patent Application No. PCT/US2016/033201 with International Filing Date May 19, 2016, (14 pages).
International Search Report and Written Opinion dated Sep. 7, 2016, for International Application No. PCT/US2016/036873 with International filing date Jun. 10, 2016, (8 pages).
Kano, 2010, Text mining meets workflow: linking U-Compare with Taverna, Bioinformatics 26(19):2486-7.
Kehr, 2014, Genome alignment with graph data structures: a comparison, BMC Bioinformatics 15:99.

Kent, 2002, BLAT—The Blast-Like Alignment Tool, Genome Research 4:656-664.
Kim, 2005, ECgene: Genome-based EST clustering and gene modeling for alternative splicing, Genome Res 15:566-576.
Kim, 2008, A Scaffold Analysis Tool Using Mate-Pair Information in Genome Sequencing, Journal of Biomedicine and Biotechnology 8(3):195-197.
Kim, 2013, TopHat2: accurate alignment of transcriptomes in the presence of insertions, deletions and gene fusions, Genome Biol 14(4):R36.
Koolen, 2008, Clinical and Molecular Delineation of the 17q21.31 Microdeletion Syndrome, J Med Gen 45(11):710-720.
Kumar, 2010, Comparing de novo assemblers for 454 transcriptome data, BMC Genomics 11:571.
Kurtz, 2004, Versatile and open software for comparing large genomes, Genome Biol 5:R12.
Lam, 2008, Compressed indexing and local alignment of DNA, Bioinformatics 24(6):791-97.
Langmead, 2009, Ultrafast and memory-efficient alignment of short DNA sequences to the human genome, Genome Biol 10:R25.
Larkin, 2007, Clustal W and Clustal X version 2.0, Bioinformatics 23(21):2947-2948.
Lecca, 2015, Defining order and timing of mutations during cancer progression: the TO-DAG probabilistic graphical model, Frontiers in Genetics, vol. 6 Article 309 1-17.
Lee et al. Accurate read mapping using a graph-based human pan-genome. (May 2015) American Society of Human Genetics 64th Annual Meeting Platform Abstracts; Abstract 41.
Lee, 2002, Multiple sequence alignment using partial order graphs, Bioinformatics 18(3):452-464.
Lee, 2003, Generating consensus sequences from partial order multiple sequence alignment graphs, Bioinformatics 19 (8):999-1008.
Lee, 2005, Bioinformatics analysis of alternative splicing, Brief Bioinf 6(1):23-33.
Lee, 2014, Accurate read mapping using a graph-based human pan-genome, ASHG 2014 Abstracts.
LeGault, 2010, Learning Probalistic Splice Graphs from RNA-Seq data, pages.cs.wisc.edu/~legault/cs760_writeup.pdf; retrieved from the internet on Apr. 6, 2014.
LeGault, 2013, Inference of alternative splicing from RNA-Seq data with probabilistic splice graphs, Bioinformatics 29 (18):2300-2310.
Leipzig, 2004, The alternative splicing gallery (ASG): Bridging the gap between genome and transcriptome, Nuc Acids Res 23(13):3977-3983.
Li, 2009, Fast and accurate short read alignment with Burrows-Wheeler Transform. Bioinformatics 25:1754-60.
Li, 2010, A survey of sequence alignment algorithms for next-generation sequencing, Briefings in Bionformatics 11 (5):473-483.
Life Technologies, 2013, Rapid Exome Sequencing Using the Ion Proton System and Ion Ampliseq Technology, Application Note (5 Pages).
Lipman, 1985, Rapid and sensitive protein similarity searches, Science 227(4693):1435-41.
Lucking, 2011, PICS-Ord: unlimited coding of ambiguous regions by pairwise identity and cost scores ordination, BMC Bioinf 12:10.
Lupski, 2005, Genomic disorders: Molecular mechanisms for rearrangements and conveyed phenotypes, PLoS Genetics 1(6):e49.
Ma, 2010, Multiple genome alignment based on longest path in directed acyclic graphs, Int J Bioinformatics 6 (4):366-683.
Mamoulis, 2004, Non-contiguous sequence pattern queries, in Advances in Database Technology—EDBT 2004: 9th International Conference on Extending Database Technology, Heraklion, Crete, Greece, Mar. 14-18, 2004, Proceedings (18 pages); retrieved from the internet on Jun. 3, 2016.
Wu, 2010, Fast and SNP-tolerant detection of complex variants and splicing in short reads, Bioinformatics, 26 (7):873-881.
Xing, 2006, An expectation-maximization algorithm for probabilistic reconstructions of full-length isoforms from splice graphs, Nucleic Acids Research, 34:3150-3160.
Yang, 2013, Leveraging reads that span multiple single nucleotide polymorphisms for haplotype inference from sequencing data, Bioinformatics 29(18):2245-2252.

(56) References Cited

OTHER PUBLICATIONS

Yanovsky, 2008, Read mapping algorithms for single molecule sequencing data, Proc 8th Int Workshop Alg Bioinformatics 5251:38-49.
Yu, 2010, The construction of a tetrapioid cotton genome wide comprehensive reference map, Genomics 95:230-240.
Zeng, 2013, PyroHMMvar: a sensitive and accurate method to call short indels and SNPs for Ion Torrent and 454 data, Bioinformatics 29:22 2859-2868.
Zhang et al., Construction of a high-density genetic map for sesame based on large scale marker development by specific length amplified fragment (SLAF) sequencing. (2013) pp. 1-12, vol. 13, BMC Plant Biology.
PCT/US2015/048891, Nov. 17, 2015, International Search Report and Written Opinion.
EP 19186646.6, Jun. 17, 2020, Extended European Search Report and Written Opinion.
PCT/US2015/054461, Jan. 5, 2016, International Search Report and Written Opinion.
Marth et al., 1999—A general approach to single-nucleotide polymorphism discovery, pp. 452-456, vol. 23, Nature Genetics.
Mazrouee, 2014, FastHap: fast and accurate single individual haplotype reconstructions using fuzzy conflict graphs, Bioinformatics 30:i371-i378.
McSherry, 2001, Spectral partitioning of random graphs, Proc 42nd IEEE Symp Found Comp Sci 529-537.
Miller, 2010, Assembly Algorithms for Next-Generation Sequencing Data, Genomics 95(6):315-327.
Mount, 2001, Multiple Sequence Alignment, Bioinformatics, 2001, Cold Spring Harbor Laboratory Press, Cold Spring Harbor, New York, pp. 139-204.
Mourad, 2012, A hierarchical Bayesian network approach for linkage disequilibrium modeling and data-dimensionality reduction prior to genome-wide association studies, BMC Bioinformatics 12:16 1-20.
Myers, The Fragment Assembly String Graph, Bioinformatics, 2005, pp. ii79-ii85, vol. 21.
Nagarajan, 2013, Sequence assembly demystified, Nat Rev 14:157-167.
Nakao, 2005, Large-scale analysis of human alternative protein isoforms: pattern classification and correlation with subcellular localization signals, Nucl Ac Res 33(8):2355-2363.
Needleman, 1970, A general method applicable to the search for similarities in the amino acid sequence of two proteins, J Mol Biol 48(3):443-453.
Newman, 2013, Community detection and graph portioning, Europhys Lett 103(2):28003, arXiv:1305.4974v1.
Newman, 2014, An ultrasensitive method for quantitating circulating tumor DNA with broad patient coverage, Nature Medicine 20:5 1-11.
Olsson, 2015, Serial monitoring of circulating tumor DNA in patients with primary breast cancer for detection of occult metastatic disease, EMBO Molecular Medicine 7:8 1034-1047.
Oshiack, 2010, From RNA-seq reads to differential expression results. Genome Bio 11:220.
Parks, 2015, Detecting non-allelic homologous recombination from high-throughput sequencing data, Genome Biol 16:17.
Peixoto, 2014, Efficient Monte Carlo and greedy heuristic for the inference of stochastic block models, Phys. Rev. E 89, 012804.
Pop et al., 2004, Comparative genome assembly, Briefings in Bioinformatics vol. 5, pp. 237-248.
Pruesse, 2012, SINA: Accurate high-throughput multiple sequence alignment of ribosomal RNA genes, Bioinformatics 28:14 1823-1829.
Rajaram, 2013, Pearl millet [*Pennisetum glaucum* (L.) R. Br.] consensus linkage map constructed using four RIL mapping populations and newly developed EST-SSRs, BMC Genomics 14(1):159.
Ramirez-Gonzalez, 2011, Gee Fu: a sequence version and webservices database tool for genomic assembly, genome feature and NGS data, Bioinformatics 27(19):2754-2755.
Raphael, 2004, A novel method for multiple alignment of sequences with repeated and shuffled elements, Genome Res 14:2336-2346.
Robertson, 2010, De novo assembly and analysis of RNA-seq data, Nat Meth 7(11):909.
Rodelsperger, 2008, Syntenator: Multiple gene order alignments with a gene-specific scoring function, Alg Mol Biol 3:14.
Rognes, 2000, Six-fold speed-up of Smith-Waterman sequence database searching using parallel processing on common microprocessors, Bioinformatics 16(8):699-706.
Rognes, 2001, ParAlign: a parallel sequence alignment algorithm for rapid and sensitive database searches, Nucl Ac Res 29(7):1647-1652.
Rognes, 2011, Faster Smith-Waterman database searches with inter-sequence SIMD parallelisation, Bioinformatics 12:221.
Ronquist, 2012, MrBayes 3.2: efficient Bayesian phylogenetic inference and model choice across a large model space, Syst Biol 61(3):539-42.
Saebo, 2005, PARALIGN: rapid and sensitive sequence similarity searches powered by parallel computing technology, Nucl Ac Res 33:W535-W539.
Sato, 2008, Directed acyclic graph kernels for structural RNA analysis, BMC (BioMed Central) Bioinformatics 9(318).
Schneeberger, 2009, Sumaltaneous alignment of short reads against multiple genomes, Genome Biol 10(9):R98.2-R98.12.
Schwikowski, 2002, Weighted sequence graphs: boosting iterated dynamic programming using locally suboptimal solutions, Disc Appl Mat 127:95-117.
Shao, 2006, Bioinformatic analysis of exon repetition, exon scrambling and trans-splicing in humans, Bioinformatics 22: 692-698.
Sievers, 2011, Fast, scalable generation of high-quality protein multiple sequence alignments using Clustal Omeag, Mol Syst Biol 7:539.
Slater, 2005, Automated generation of heuristics for biological sequence comparison, BMC Bioinformatics 6:31.
Smith, 2012, Multiple insert size paired-end sequencing for deconvolution of complex transcriptions, RNA Bio 9(5) 596-609.
Sosa, 2012, Next-Generation Sequencing of Human Mitochondrial Reference Genomes Uncovers High Heteroplasmy Frequency, PLoS One 8(10):e1002737.
Sturgeon, RCDA: a highly sensitive and specific alternatively spliced transcript assembly tool featuring upstream consecutive exon structures, Genomics, Dec. 2012, 100(6): 357-362.
Subramanian, 2008, DIALIGN-TX: greedy and progessive approaches for segment-based multiple sequence alignment, Alg Mol Biol 3(1):1-11.
Sudmant, 2015, An integrated map of structural variation in 2,504 human genomes, Nature 526:75-81.
Sun, 2006, Pairwise Comparison Between Genomic Sequences and Optical maps, dissertation, New York University (131 pages); retreived from the internet on Jun. 3, 2016.
Szalkowski, 2012, Fast and robust multiple sequence alignment with phylogeny-aware gap placement, BMC (BioMed Central) Bioinformatics 13(129).
Szalkowski, 2013, Graph-based modeling of tandem repeats improves global multiple sequence alignment, Nucl Ac Res 41(17):e162.
Tarhio, 1993, Approximate Boyer-Moore String Matching, Siam J Comput 22(2):243-260.
Thomas, 2014, Community-wide effort aims to better represent variation in human reference genome, Genome Web (11 pages).
Trapnell, 2009, TopHat: discovering splice junctions with RNA-Seq, Bioinformatics 25:1105-1111.
Trapnell, 2010, Transcript assembly and abundance estimation from RNA-Seq reveals thousands of new transcripts and switching among isoforms, Nat Biotech 28(5):511-515.
Trapnell, 2010, Transcript assembly and quantification by RNA-Seq reveals unannotated transcripts and isoform switching during cell differentiation, Nat Biotech 28(5):511-515.
Uchiyama et al., CGAT: a comparative genome analysis tool for visualizing alignments in the analysis of complex evolutionary changes between closely related genomes, 2006, e-pp. 1-17, vol. 7:472; BMC Bioinformatics.
Wang, 2009, RNA-Seq: a revolutionary tool fortranscriptomics, Nat Rev Genet 10(1):57-63.

(56) References Cited

OTHER PUBLICATIONS

Written Opinion issued in SG 11201601124Y.
Extended European Search Report for European Application No. 19186646.6 dated Jun. 17, 2020.
International Search Report and Written Opinion for International Application No. PCT/US2015/054461 dated Jan. 5, 2016.
International Search Report and Written Opinion for International Application No. PCT/US2015/048891 dated Nov. 17, 2015.
Abouelhoda, 2012, Tavaxy: integrating Taverna and Galaxy workflows with cloud computing support, BMC Bioinformatics 13:77.
Attolini et al., A mathematical framework to determine the temporal sequence of somatic genetic events in cancer. Proceedings of the National Academy of Sciences. Oct. 12, 2010;107(41):17604-9.
BCF2 Quick Reference (r198), available at http://samtools.github.io/hts-specs/BCFv2_qref.pdf., 2020.
Bertone, 2004, Global Identification of human transcribed sequences with genome tiling arrays; Science 306:2242-2246.
Buhler, 2001, Search algorithms for biosequences using random projection, dissertation, University of Washington (203 pages); retreived from the internet on Jun, 3, 2016.
Carrington, 1985, Polypeptide ligation occurs during post-translational modification of concanavalin A, Nature 313:64-67.
Clark, 2014, Illumina announces landmark $1,000 human genome sequencing, Wired, Jan. 15, 2014.
Cock, 2013, Galaxy tools and workflows for sequence analysis with applications in molecular plant pathology, Peer J 1: e167.
Cohen-Boulakia, 2014, Distilling structure in Taverna scientific workflows: a refactoring approach, BMC Bioinformatics 15(Suppl 1):S12.
Costa, 2010, Uncovering the Complexity of Transcriptomes with RNA-Seq, J Biomed Biotech 853916.
Danecek, 2011, The variant call format and VCFtools, Bioinformatics 27(15):2156-2158.
Delcher, 1999, Alignment of whole genomes, Nucl. Acids Res 27(11):2369-76.
Durham, 2005, EGene: a configurable pipeline system for automated sequence analysis, Bioinformatics 21(12):2812-2813.
Fiers, 2008, High-throughput Bioinformatics with the Cyrille2 Pipeline System, BMC Bioinformatics 9:96.
Florea, 2005, Gene and alternative splicing annotation with AIR, Genome Res 15:54-66.
Glusman, 2014, Whole-genome haplotyping approaches and genomic medicine, Genome Med 6:73.
Goto, 2010, BioRuby: bioinformatics software for the Ruby programming language, Bioinformatics 26(20):2617-2619.
Gu, Revealing the functional cooperation among cancer-related pathways based on mutation profiles of cancer genomes. China Doctoral Dissertation Full-text Database, Medical Science and Technology, May 2011;1: E072-11.
Hokamp, 2003, Wrapping up BLAST and Other Applications for Use on Unix Clusters, Bioinformatics 19(3)441-42.
Holland, 2008, Bio Java: an open-source framework for bioinformatics, Bioinformatics 24(18):2096-2097.
Hoon, 2003, Biopipe: A flexible framework for protocol-based bioinformatics analysis, Genome Res 13(8):1904-1915.
Hull, 2006, Taverna: a tool for building and running workflows of services, Nucl Acids Res 34(Web Server Issue): W729-32.
International HapMap Consortium, 2005, A haplotype map of the human genome. Nature 437:1299-1320.
Katoh, 2005, MAFFT version 5: improvement in accuracy of multiple sequence alignment, Nucl Acids Res 33(2):511-518.
Kawas, 2006, BioMoby extensions to the Taverna workflow management and enactment software, BMC Bioinformatics 7:523.
Krabbenhoft, 2008, Integrating ARC grid middleware with Taverna workflows, Bioinformatics 24(9):1221-2.
Kuhn, 2010, CDK-Taverna: an open workflow environment for cheminformatics, BMC Bioinformatics 11:159.
LaFramboise, 2009, Single nucleotide polymorphism arrays: a decade of biological, computational and technological advance, Nucleic Acids Res 37(13):4181-4193.
Layer, 2015, Efficient genotype compression and analysis of large genetic-variation data sets, Nat Meth 13(1):63-65.
Lee, 2014, Mosaik: A hash-based algorithm for accurate next-generation sequencing short-read mapping, PLoS One 9(3):e90581.
Li, 2008, Automated manipulation of systems biology models using libSBML within Taverna workflows, Bioinformatics 24(2):287-9.
Li, 2008, Performing statistical analyses on quantitative data in Taverna workflows: an example using R and maxdBrowse to identify differentially-expressed genes from microarray data, BMC Bioinformatics 9:334.
Li, 2008, SOAP: short oligonucleotide alignment program, Bioinformatics 24(5):713-14.
Li, 2009, SOAP2: an improved ultrafast tool for short read alignment, Bioinformatics 25(15):1966-67.
Li, 2009, The Sequence Alignment/Map format and SAMtools, Bioinformatics 25(16):2078-9.
Li, 2015, BGT: efficient and flexible genotype query across many samples, arXiv:1506.08452 [q-bio. GN].
Li, 2015, Towards Better Understanding of Artificats in Variant Calling from High-Coverage Samples, arXiv:1404,0929 [q-bio. GN].
Lindgreen, 2012, AdapterRemoval: easy cleaning of next-generation sequence reads, BMC Res Notes 5:337.
Manolio, 2010, Genome wide association studies and assessment of the risk of disease, NEJM 363(2):166-76.
Mardis, 2010, The $1,000 genome, the $100,000 analysis?, Genome Med 2:84-85.
Margulies, 2005, Genome sequencing in micro-fabricated high-density picotiter reactors, Nature 437:376-380.
McKenna, 2010, The Genome Analysis Toolkit: a MapReduce framework for analyzing next-generation DNA sequencing data, Genome Res 20(9):1297-1303.
Misra, 2011, Anatomy of a hash-based long read sequence mapping algorithm for next generation DNA sequencing, Bioinformatics 27(2):189-195.
Missier, 2010, Taverna, reloaded, Proc. Scientific and Statistical Database Management, 22nd Int Conf, Heidelberg, Germany, Jun./Jul. 2010, Gertz & Ludascher, Eds., Springer.
Moudrianakis, 1965, Base sequence determination in nucleic acids with electron microscope III: chemistry and microscopy of guanine-labelled DNA, PNAS 53:564-71.
Nagalakshmi, 2010, RNA-Seq: A Method for Comprehensive Transcriptome Analysis, Curr Proc Mol Biol 4.11.1.13.
Najafi, 2016, Fundamental limits of pooled-DNA sequencing, arXiv:1604.04735.
Nenadic, 2010, Nested Workflows, The Taverna Knowledge Blog, Dec. 13, 2010. Retrieved on Feb. 25, 2016 from http://taverna.knowledgeblog.org/2010/12/13/nested-workflows/.
Ning, 2001, SSAHA: a fast search method for large DNA databases, Genome Res 11(10):1725-9.
Oinn, 2006, Taverna: lessons in creating a workflow environment for the life sciences, Concurrency and Computation: Practice and Experience 18(10)1067-1100.
O'Rawe, 2013, Low Concordance of Multiple Variant-Calling Pipelines: Practical Implications for Exome and Genome Sequencing, Genome Med 5:28.
Pabinger, 2013, A survey of tools for variant analysis of next-generation genome sequencing data, Brief Bioinf.
Paterson, 2009, An XML transfer schema for exchange of genomic and genetic mapping data: Implementation as a web service in a Taverna workflow, BMC Bioinformatics 10:252.
Pearson, 1988, Improved tools for biological sequence comparison, PNAS 85(8):2444-8.
Pe'er, 2006, Evaluating and improving power in whole-genome association studies using fixed marker sets. Nat Genet 38:663-667.
Pope, 2014, ROVER Variant Caller: Read-Pair Overlap Considerate Variant-Calling Software Applied to PCR-Based Massively Parallel Sequencing Datasets, Source Code Bio Med 9:3.
Popitsch, 2013, NGC: lossless and lossy compression of aligned high-throughput sequencing data, Nucl Acids Res, 41(1):e27.
Posada, 1998, Model Test: testing the model of DNA substitution, Bioinformatics 14(9):817-8.

(56) References Cited

OTHER PUBLICATIONS

Potter, 1994, ASC: An Associative-Computing Paradigm, Computer 27(11):19-25.
Potter, 2004, The ensemble analysis pipeline, Genome Res 14:934-941.
Quail, et al., 2012, A tale of three next generation sequencing platforms: comparison of Ion Torrent, Pacific Biosciences and Illumina MiSeq sequencers, BMC Genomics 13:341.
Rothberg, 2011, An integrated semiconductor device enabling non-optical genome sequencing, Nature 475:348-352.
Schenk, 2013, A pipeline for comprehensive and automated processing of electron diffraction data in IPLT, J Struct Biol 182(2):173-185.
Smith, 1981, identification of common molecular subsequences, J Mol Biol, 147(1):195-197.
Soni, 2007, Progress toward ultrafast DNA sequencing using solid-state nanopores, Clin Chem 53(11):1996-2001.
Sroka, 2006, XQTav: an XQuery processor for Taverna environment, Bioinformatics 22(10):1280-1.
Sroka, 2010, A formal semantics for the Taverna 2 workflow model, J Comp Sys Sci 76(6):490-508.
Sroka, 2011, CalcTav—integration of a spreadsheet and Taverna workbench, Bioinformatics 27(18):2618-9.
Stephens, 2001, A new statistical method for haplotype reconstruction from population data, Am J Hum Genet 68:978-989.
Stewart, 2011, A comprehensive map of mobile element insertion polymorphisms in humans, PLoS Genetics 7(8):1-19.
Tan, 2010, A Comparison of Using Taverna and BPEL in Building Scientific Workflows: the case of caGrid, Concurr Comput 22(9): 1098-1117.
Tan, 2010, CaGrid Workflow Toolkit: a Taverna based workflow tool for cancer grid, BMC Bioinformatics 11:542.
Tewhey, 2011, The importance of phase information for human genomics, Nat Rev Gen 12:215-223.
The 1000 Genomes Project, 2015, A global reference for human genetic variation, Nature 526:68-74.
The Variant Call Format (VCF) Version 4.2 Specification (Jan. 26, 2015), available at https://samtools.github.io/hts-specs/VCFv4.2.pdf.
The Wellcome Trost Case Control Consortium, Genome-wide association study of 14,000 cases of seven common diseases and 3,000 shared controls, Nature, 447 (7145), pp. 661-678.
Torri, 2012, Next generation sequence analysis and computational genomics using graphical pipeline workflows, Genes (Basel) 3(3):545-575.
Truszkowski, 2011, New developments on the cheminformatics openworkflow environment CDK-Taverna, J Cheminform 3:54.
Turi, 2007, Taverna Workflows: Syntax and Semantics, IEEE Int Conf on e-Science and Grid Computing 441-448.
Wallace et al., 2005, Multiple sequence alignments, Curr Op Struct Biol 15(3):261-266.
Wang, 2011, Next sequencing has lower sequence coverage and poorer SNP-detection capability in the regulatory regions, Scientific Reports 1:55.
Wassink, 2009, Using R in Taverna: RShell v1.2. BMC Res Notes 2:138.
Waterman, 1976, Some biological sequence metrics, Adv Math 20(3):367-387.
Wei, Estrogen Receptor K303R Mutation and Breast Cancer Occurrence and Progress. China Excellent Master's Thesis Full-text Database, Medical Health Science and Technology. Mar. 20, 2004;4:42 pages.
Wolstencroft, 2005, Panoply of Utilities in Taverna, Proc 2005 1st Int Conf e-Science and Grid Computing 156-162.
Wolstencroft, 2013, The Taverna Workflow Suite: Designing and Executing Workflows of Web Services on the Desktop, Web or in the Cloud, Nucl Acids Res 41(W1):W556-W561.
Yang, 2014, Community detection in networks with node attributes, proc IEEE ICDM '13, arXiv:1401.7267.
Yildiz, 2014, BIFI: a Taverna plugin for a simplified and user-friendly workflow platform, BMC Res Notes 7:740.
Yu, 2007, A tool for creating and parallelizing bioinformatics pipelines, DOD High Performance Computing Conf 417-420.
Zhang, 2013, Taverna Mobile: Tavema workflows on Android, EMBnet J 19(B):43-45.
Zhao, 2012, Why Workflows Break-Understanding and Combating Decay in Taverna Workflows, eScience 2012, Chicago, Oct. 2012.
Extended European Search Report for European Application No. 14837955.5 dated Mar. 29, 2017.
Extended European Search Report for European Application No. 14847490.1 dated May 9, 2017.
Extended European Search Report for European Application No. 14854801.9 dated Apr. 12, 2017.
Communication Pursuant to Article 94(3) EPC for European Application No. 14803268.3 dated Apr. 21, 2017.
Written Opinion issued in Singapore Application No. 11201601124Y dated Dec. 21, 2016.
Written Opinion issued in Singapore Application No. 11201602903X dated May 29, 2017.
Written Opinion issued in Singapore Application No. 11201603039P dated Jun. 12, 2017.
Written Opinion issued in Singapore Application No. 11201603044S dated Jul. 10, 2017.
Written Opinion issued in Singapore Application No. 11201605506Q dated Jun. 15, 2017.
International Preliminary Report on Patentability for International Application No. PCT/US2014/052065 dated Mar. 3, 2016.
Chen et al., Transient hypermutability, chromothripsis and replication-based mechanisms in the generation of concurrent clustered mutations. Mutation Research/Reviews in Mutation Research. Jan. 1, 2012;750(1):52-9.
Denœud et al., Identification of polymorphic tandem repeats by direct comparison of genome sequence from different bacterial strains: a web-based resource. BMC bioinformatics. Dec. 2004;5(1):1-2.
Golub et al., Molecular classification of cancer: class discovery and class prediction by gene expression monitoring, science. Oct. 15, 1999;286(5439):531-7.
Harenberg et al., Community detection in large-scale networks: a survey and empirical evaluation. Wiley Interdisciplinary Reviews: Computational Statistics. Nov. 2014;6(6):426-39.
Oinn et al., Taverna: a tool for the composition and enactment of bioinformatics workflows. Bioinformatics. Nov. 22, 2004;20(17):3045-54.

\* cited by examiner

Sequence Examples

1) SEQ ID NO. 12: CCCAGAACGTTGCATCGTAGACGAGTTTCAGCATT

2) SEQ ID NO. 13: CCCAGAACGTTGCTATGCAACAAGGGACATCGTAGACGAGTTTCAGCATT
3) SEQ ID NO. 14: CCCAGAACGTTGCTATGCAGGAAGGGACATCGTAGACGAGTTTCAGCATT insertion / polymorphism associated with cancer

SEQUENCE LISTING

```
<160> NUMBER OF SEQ ID NOS: 16

<210> SEQ ID NO 1
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 1
catagtacct aggtcttgga gctagtc                                    27

<210> SEQ ID NO 2
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 2
catagtacct aggtcttggc tagtc                                      25

<210> SEQ ID NO 3
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 3
catagtacct agggtcttg gctagtc                                     27

<210> SEQ ID NO 4
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 4
catagtacct agggtcttg gagctagtc                                   29

<210> SEQ ID NO 5
<211> LENGTH: 25
```

```
<212> TYPE: DNA
<213> ORGANISM: Artificial Sequence
<220> FEATURE:
<223> OTHER INFORMATION: Synthetic Sequence

<400> SEQUENCE: 5
cataggacct aggtcttggc tagtc                                            25

<210> SEQ ID NO 6
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 6
cataggacct aggtcttgga gctagtc                                          27

<210> SEQ ID NO 7
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 7
cataggacct aggggtcttg gctagtc                                          27

<210> SEQ ID NO 8
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 8
cataggacct aggggtcttg gagctagtc                                        29

<210> SEQ ID NO 9
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 9
ggatcgaaat gg                                                          12

<210> SEQ ID NO 10
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 10
ttggatcgaa ttatggg                                                     17

<210> SEQ ID NO 11
<211> LENGTH: 11
<212> TYPE: DNA
<213> ORGANISM: Artificial Sequence
<220> FEATURE:
<223> OTHER INFORMATION: Synthetic Sequence

<400> SEQUENCE: 11
```
ttggatatgg g                                                          11

<210> SEQ ID NO 12
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 12
cccagaacgt tgcatcgtag acgagtttca gcatt                                35

<210> SEQ ID NO 13
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 13
cccagaacgt tgctatgcaa caagggacat cgtagacgag tttcagcatt                50

<210> SEQ ID NO 14
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 14
cccagaacgt tgctatgcag gaagggacat cgtagacgag tttcagcatt                50

<210> SEQ ID NO 15
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 15
agctacgtac actacc                                                     16

<210> SEQ ID NO 16
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 16
agctatcgta ctagc                                                      15

METHODS AND SYSTEMS FOR DETECTING SEQUENCE VARIANTS

RELATED APPLICATIONS

This application is a continuation of U.S. patent application Ser. No. 14/517,451, filed Oct. 17, 2014 (now U.S. Pat. No. 10,053,736), which claims priority to U.S. Patent Application No. 61/892,670, filed Oct. 18, 2013, each of which are incorporated by reference herein in their entireties.

SEQUENCE LISTING

This application contains a sequence listing which has been submitted in ASCII format via EFS-Web and is hereby incorporated by reference in its entirety. The ASCII-formatted sequence listing, created on Jan. 18, 2019, is named SBG-008-02USSequences_ST25.txt, and is 3,584 bytes in size.

FIELD OF THE INVENTION

The invention relates to methods and systems for identifying disease-induced mutations, such as caused by cancer. The invention additionally provides methods for identifying mutations that may be causative of advanced disease, such as metastatic cancers.

BACKGROUND

Many diseases result from inherited or random mutations in a patient's genetic sequence. Additionally, in diseases such as cancer, advanced stages of disease may manifest as new changes in the genetic sequence of diseased cells. Accordingly, there is increased interest in sequencing diseased cells, e.g., from a biopsy or freely circulating, to determine the type or stage of a disease. Thus, patients who have undergone treatment for a disease may have new biopsy samples sequenced to monitor disease recurrence and/or progression. Such monitoring allows for early intervention in the event of recurrence, and also avoids unnecessary treatment when changes are not detected.

While there are many diseases that can be typed and tracked with genetic screening, cancer mutation screening has received the most attention. In some instances, the type of cancer can be immediately identified because of one tell-tale mutation, such as BRCA1. In most instances, however, cancer typing involves discovering and analyzing several sequences from a patient. Because these samples originate from the same patient, the samples are not independent of each other, but rather, are interrelated both developmentally and structurally. Furthermore, in most instances, accurate typing of a tumor requires knowledge of three sequences: the subject's healthy sequence (as found in non-cancerous parts of the body), the sequence of a major cancerous clone, and the sequences of minor clones (which may often be metastatic).

The prospect of sequencing several samples to obtain a complete picture of a disease is less intimidating due to recent advances in genetic sequencing. Next-generation sequencing (e.g., whole-transcriptome shotgun sequencing, pyrosequencing, ion semiconductor sequencing, sequencing by synthesis) can generate millions of reads, covering an entire genome, in just a few days. To achieve this throughput, NGS sequencing uses massive parallelization on smaller nucleic acid sequences that together make up a larger body of genetic information, e.g., a chromosome or a genome. Starting from a genetic sample, the nucleic acids (e.g., DNA) are broken up, amplified, and read with extreme speed. Once the reads are produced, the reads are aligned to a reference genome, e.g., GRCh37, with a computer to produce longer, assembled sequences, known as contigs. Because the sequence data from next generation sequencers often comprises millions of shorter sequences that together represent the totality of the target sequence, aligning the reads is complex and computationally expensive. Additionally, in order to minimize sequence distortions caused by random sequencing errors (i.e., incorrect sequencing machine outputs), each portion of the probed sequence is sequenced multiple times (e.g., 2 to 100 times, or more) to minimize the influence of any random sequencing errors on the final alignments and output sequences generated.

Once all of the data, corresponding to all of the nucleic acid reads is collected, and the reads are aligned against the reference, the reads are assembled and compared to the reference, as well as to each other, to determine the relationship between the samples. The workflow for this analysis is shown pictorially in FIG. 1. Each assembled read is typically compared to the reference whereupon the variations between the assembled sequence and the reference are cataloged in a file, known as a variant file, which may be in one of several accepted formats.

These variant files can then be compared to each other, in order to determine how different the genetic material varies between cells with varying stages of the disease. The variant files can also be the basis for later comparison with new samples from the patient to screen for recurrence or disease progression.

The workflow illustrated in FIG. 1 suffers from several drawbacks. Because there may be millions of genetic differences between the reference sequence and the sequences of the samples of the patient, it is often very difficult to pinpoint the key differences between the non-diseased and diseased tissues. In theory, this problem can be avoided by comparing the sequences of the diseased and non-diseased samples directly, however the use of the reference sequence for the original alignment "infects" the downstream analysis. Typically, certain portions of the patient's samples that did not align with the reference are treated as equivalent mutations in the variant files, even though they are not, in fact, equivalent. Furthermore, structural variations between the reference sequence and the patient's samples, and between the patient's samples themselves, result in variant files with differing indexes for the same (or similar) mutations. Especially in the instance of recurrence screening, the lack of a stable index makes it very difficult to identify new smaller mutations.

Typically a sequence alignment is constructed by aggregating pairwise alignments between two linear strings of sequence information, one of which is a standard reference. As an example of alignment, two strings, S1 (SEQ ID NO. 15: AGCTACGTACACTACC) and S2 (SEQ ID NO. 16: AGCTATCGTACTAGC) can be aligned against each other. S1 typically corresponds to a read and S2 correspond to a portion of the reference sequence. With respect to each other, S1 and S2 can consist of substitutions, deletions, and insertions. Typically, the terms are defined with regard to transforming string S1 into string S2: a substitution occurs when a letter or sequence in S2 is replaced by a different letter or sequence of the same length in S1, a deletion occurs when a letter or sequence in S2 is "skipped" in the corresponding section of S1, and an insertion occurs when a letter or sequence occurs in S1 between two positions that are adjacent in S2. For example, the two sequences S1 and S2 can be aligned as below. The alignment below represents thirteen matches, a deletion of length one, an insertion of length two, and one substitution:

```
(S1) AGCTA-CGTACACTACC      (SEQ ID NO. 15)

(S2) AGCTATCGTAC--TAGC      (SEQ ID NO. 16)
```

One of skill in the art will appreciate that there are exact and approximate algorithms for sequence alignment. Exact algorithms will find the highest scoring alignment, but can be computationally expensive. The two most well-known exact algorithms are Needleman-Wunsch (*J Mol Biol*, 48(3): 443-453, 1970) and Smith-Waterman (*J Mol Biol*, 147(1): 195-197, 1981; *Adv. in Math.* 20(3), 367-387, 1976). A further improvement to Smith-Waterman by Gotoh (*J Mol Biol*, 162(3), 705-708, 1982) reduces the calculation time from $O(m^2n)$ to $O(mn)$ where m and n are the sequence sizes being compared and is more amendable to parallel processing. In the field of bioinformatics, it is Gotoh's modified algorithm that is often referred to as the Smith-Waterman algorithm. Smith-Waterman approaches are being used to align larger sequence sets against larger reference sequences as parallel computing resources become more widely and cheaply available. See, e.g., Amazon.com's cloud computing resources available at aws.amazon.com. All of the above journal articles are incorporated herein by reference in their entireties.

The Smith-Waterman (SW) algorithm aligns linear sequences by rewarding overlap between bases in the sequences, and penalizing gaps between the sequences. Smith-Waterman also differs from Needleman-Wunsch, in that SW does not require the shorter sequence to span the string of letters describing the longer sequence. That is, SW does not assume that one sequence is a read of the entirety of the other sequence. Furthermore, because SW is not obligated to find an alignment that stretches across the entire length of the strings, a local alignment can begin and end anywhere within the two sequences.

The SW algorithm is easily expressed for an n×m matrix H, representing the two strings of length n and m, in terms of equation (1) below:

$$H_{k0}=H_{0l}=0 \text{ (for } 0 \leq k \leq n \text{ and } 0 \leq l \leq m)$$

$$H_{ij}=\max\{H_{i-1,j-1}+s(a_i,b_j),H_{i-1,j}-W_{in},H_{i,j-1}-W_{del},0\} \quad (1)$$
$$\text{(for } 1 \leq i \leq n \text{ and } 1 \leq j \leq m)$$

In the equations above, $s(a_i, b_j)$ represents either a match bonus (when $a_i=b_j$) or a mismatch penalty (when $a_i \neq b_j$), and insertions and deletions are given the penalties $W_{in}$ and $W_{del}$, respectively. In most instances, the resulting matrix has many elements that are zero. This representation makes it easier to backtrace from high-to-low, right-to-left in the matrix, thus identifying the alignment.

Once the matrix has been fully populated with scores, the SW algorithm performs a backtrack to determine the alignment. Starting with the maximum value in the matrix, the algorithm will backtrack based on which of the three values ($H_{i-1,j-1}$, $H_{i-1,j}$, or $H_{i,j-1}$) was used to compute the final maximum value for each cell. The backtracking stops when a zero is reached. See, e.g., FIG. 4B, which does not represent the prior art, but illustrates the concept of a backtrack, and the corresponding local alignment when the backtrack is read. Accordingly, the "best alignment," as determined by the algorithm, may contain more than the minimum possible number of insertions and deletions, but will contain far less than the maximum possible number of substitutions.

When applied as SW or SW-Gotoh, the techniques use a dynamic programming algorithm to perform local sequence alignment of the two strings, S and A, of sizes m and n, respectively. This dynamic programming technique employs tables or matrices to preserve match scores and avoid recomputation for successive cells. Each element of the string can be indexed with respect to a letter of the sequence, that is, if S is the string ATCGAA, S[1]=A, S[4]=G, etc. Instead of representing the optimum alignment as $H_{i,j}$ (above), the optimum alignment can be represented as B[j,k] in equation (2) below:

$$B[j,k]=\max(p[j,k],I[j,k],d[j,k],0) \text{ (for } 0 \leq j \leq m, 0 \leq k \leq n) \quad (2)$$

The arguments of the maximum function, B[j,k], are outlined in equations (3)-(5) below, wherein MISMATCH_PENALTY, MATCH_BONUS, INSERTION_PENALTY, DELETION_PENALTY, and OPENING_PENALTY are all constants, and all negative except for MATCH_BONUS. The match argument, p[j,k], is given by equation (3), below:

$$p[j,k]=\max(p[j-1,k-1],i[j-1,k-1],d[j-1,k-1])+\text{MISMATCH\_PENALTY, if } S[j] \neq A[k]=\max(p[j-1,k-1],i[j-1,k-1],d[j-1,k-1])+\text{MISMATCH\_BONUS, if } S[j]=A[k] \quad (3)$$

the insertion argument i[j,k], is given by equation (4), below:

$$i[j,k]=\max(p[j-1,k]+\text{OPENING\_PENALTY},i[j-1,k],d[j-1,k]+\text{OPENING\_PENALTY})+\text{INSERTION\_PENALTY} \quad (4)$$

and the deletion argument d[j,k], is given by equation (5), below:

$$d[j,k]=\max(p[j,k-1]+\text{OPENING\_PENALTY},i[j,k-1]+\text{OPENING\_PENALTY},d[j,k-1])+\text{DELETION\_PENALTY} \quad (5)$$

For all three arguments, the [0,0] element is set to zero to assure that the backtrack goes to completion, i.e., p[0,0]=i[0,0]=d[0,0]=0.

The scoring parameters are somewhat arbitrary, and can be adjusted to achieve the behavior of the computations. One example of the scoring parameter settings (Huang, Chapter 3: *Bio-Sequence Comparison and Alignment*, ser. *Curr Top Comp Mol Biol*. Cambridge, Mass.: The MIT Press, 2002) for DNA would be:

MATCH_BONUS: 10
MISMATCH_PENALTY: −20
INSERTION_PENALTY: −40
OPENING_PENALTY: −10
DELETION_PENALTY: −5

The relationship between the gap penalties (INSERTION_PENALTY, OPENING_PENALTY) above help limit the number of gap openings, i.e., favor grouping gaps together, by setting the gap insertion penalty higher than the gap opening cost. Of course, alternative relationships between MISMATCH_PENALTY, MATCH_BONUS, INSERTION_ PENALTY, OPENING_PENALTY and DELETION_PENALTY are possible.

Once the alignment is complete, the aligned sequences can be assembled to produce a sequence that can be compared to a reference (i.e., a genetic standard) to identify variants. The variants can provide insight regarding diseases, stages of disease, recurrence and the like. In the case of amino acid alignments, the assembled amino acid sequences can be compared to a standard to determine evolutionary information about the protein, or functional information about the protein. This standard method of disease comparison is time consuming, however, because many of the variants are not necessarily correlated with a disease. For example, when the genetic standard is from a population having an ancestry different from the sample, many of the called variants are due to differences in things like hair color, skin color, etc.

While the alignment methods, described above, have been useful for assembling reads produced with next-generation sequencing techniques, they are complex and time-consuming. Additionally, these techniques are ill-suited for identifying the important nuances between diseased cells of varying disease states because the uncertainty due to aligning the reads to a common reference often drowns out small changes in the genome.

SUMMARY

The invention provides improved methods and systems for identifying mutations that are induced by, or associated with, disease, especially cancer. The methods allow specific changes associated with advanced stages of the disease to be easily differentiated from lesser diseased cells, thus providing insight into the relationship between the size and location of the mutations and progression of the disease. This insight can be used to identify disease progression in other patients, and the relationship also provides for faster and more accurate typing of samples later collected from the same patient to monitor for disease progression or recurrence.

The invention employs multi-dimensional reference sequence constructs and alignment algorithms that allow new sequence samples to be simultaneously compared to multiple sequences relevant to the disease, thereby providing increased speed and accuracy in disease identification and typing. Furthermore, the reference sequence constructs of the invention accommodate structural variations, deletions, insertions, and polymorphisms between samples in a straightforward way, allowing a single construct to be assembled spanning an entire chromosome or the whole genome of a patient. Using a "look-back" type analysis, the described algorithms can also be used to align new reads in a multi-dimensional space including elements from sequences of various states of disease progression to provide more accurate alignment of sequence reads, while achieving lower error rates. Alternatively, constructs of the invention can be used to identify and/or study variations between individuals or cohorts having similar disease stages. In an embodiment, the invention is implemented by aligning sequence reads to a series of directed, acyclic sequences spanning branch points that account for sequence variation in the samples, including insertions, deletions, and substitutions. Such constructs, often represented as directed acyclic graphs (DAGs) can be assembled from existing variable sequence files or the constructs can be fabricated de novo using a standard reference as a starting point.

Once a sequence construct has been fabricated to account for sequence variation among differently diseased samples, those constructs can be used to identify disease risk in new samples from the same individual or, in some instances, from other individuals. In particular, because portions of the sequence construct can be tagged with secondary information, such as "metastatic," the subsequent step of comparing a mutation, vis-à-vis the reference genome, to a table of known mutations can be eliminated. Thus, it is merely a matter of identifying a sample as being aligned to sequences in the construct that are indicative of the disease or stage. Alternatively, when a mutation is not known (i.e., not represented in the reference sequence construct), an alignment will be found, whereby the variant can be identified as a new mutation. Thus, using this iterative process, it is possible to compare and/or identify differences between major and minor cancer clones, or between pre-cancerous and cancerous samples.

The invention additionally includes systems for executing the methods of the invention. In one embodiment, a system comprises a distributed network of processors and storage capable of comparing a plurality of sequences (i.e., nucleic acid sequences, amino acid sequences) to a reference sequence construct (e.g., a DAG) representing observed variation in a genome or a region of a genome. The system is additionally capable of aligning the nucleic acid reads to produce a continuous sequence using an efficient alignment algorithm. Because the reference sequence construct compresses a great deal of redundant information, and because the alignment algorithm is so efficient, the reads can be tagged and assembled on an entire genome using commercially-available resources. The system comprises a plurality of processors that simultaneously execute a plurality of comparisons between a plurality of reads and the reference sequence construct. The comparison data may be accumulated and provided to a health care provider. Because the comparisons are computationally tractable, analyzing sequence reads will no longer represent a bottleneck between NGS sequencing and a meaningful discussion of a patient's genetic risks.

BRIEF DESCRIPTION OF THE FIGURES

FIG. 2A shows the starting reference sequence and the addition of a deletion. FIG. 2B shows the addition of an insertion and a SNP, thus arriving at the Final DAG used for alignment;

FIG. 4A shows a pictorial representation of aligning a nucleic acid sequence read against a construct that accounts for an insertion event as well as the reference sequence;

FIG. 4B shows the matrices and the backtrack used to identify the proper location of the nucleic acid sequence read "ATCGAA";

DETAILED DESCRIPTION

Figure 1:
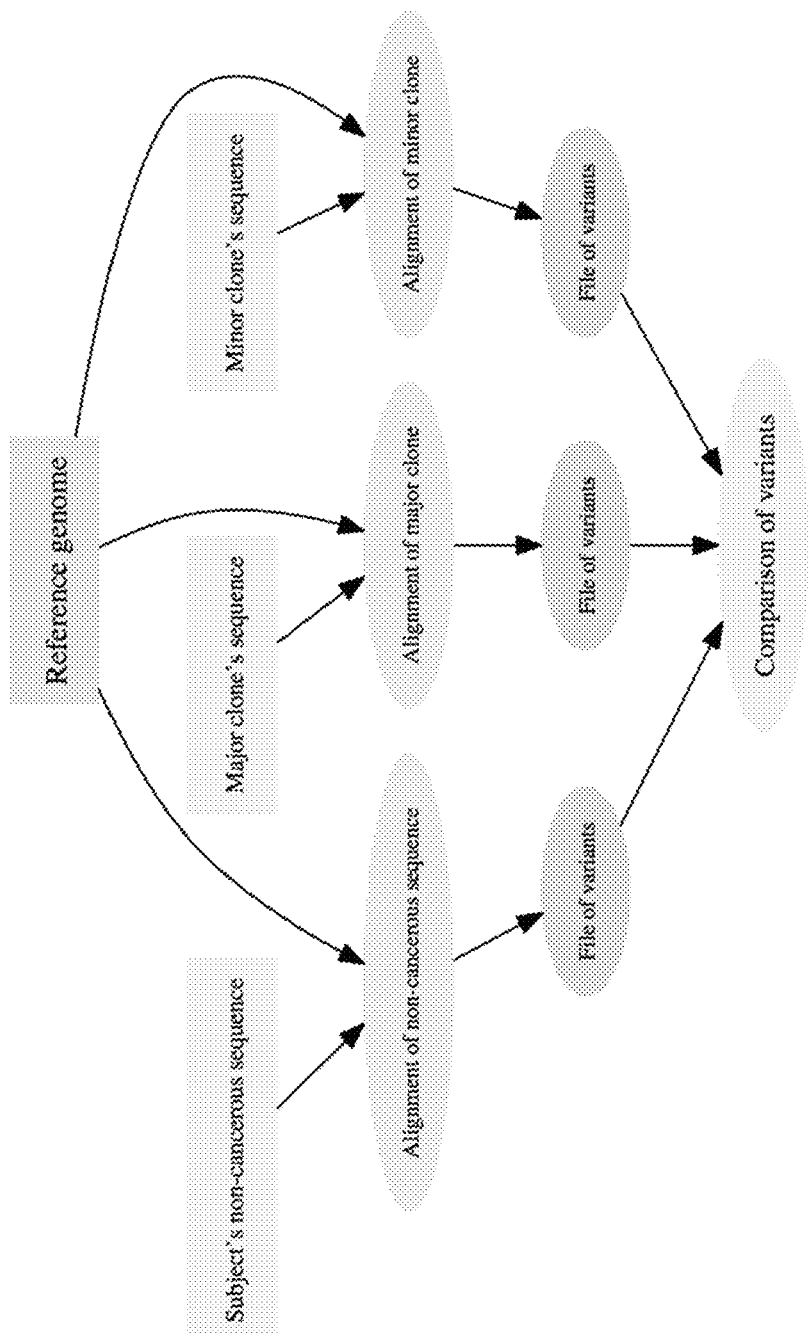
FIG. 1 depicts the state-of-the-art methods for aligning sequence reads to a reference sequence, identifying variant files, and then comparing variant files to determine variations associated with disease types or disease progression.

The invention includes methods and systems for identifying diseased-induced mutations by producing multi-dimensional reference sequence constructs that account for variations between individuals, different diseases, and different stages of those diseases. Once constructed, these reference sequence constructs can be used to align sequence reads corresponding to genetic samples from patients suspected of having a disease, or who have had the disease and are in suspected remission. The aligned sequences give immediate information about the nature of the samples, e.g., being of a metastatic nature. Thus, the reference sequence constructs can be used to monitor patients for recurrence or progression of a disease, such as cancer. The reference sequence constructs can also be used to study structural relationships between diseases and/or between disease states. The reference sequence constructs can be fabricated from previously determined variant files, or the reference sequence constructs can be created de nova, e.g., from samples originating from a patient.

In some embodiments, the reference sequence constructs are directed acyclic graphs (DAG), as described below, however the reference sequence can be any representation reflecting genetic variability in the sequences of different organisms within a species, provided the construct is formatted for alignment. The genetic variability represented in the construct may be between different tissues or cells within an individual. The genetic variability represented in the construct may be between different individuals or between different organisms. The genetic variability represented in the construct may be between similar tissues or cells that are at different stages of a disease.

In general, the reference sequence construct will comprise portions that are identical and portions that vary between sampled sequences. Accordingly, the constructs can be thought of as having positions (i.e., according to some canonical ordering) that comprise the same sequence(s) and some positions that comprise alternative sequences, reflecting genetic variability. The application additionally discloses methods for identifying a disease or a disease stage based upon alignment of a nucleic acid read to a location in the construct. The methods are broadly applicable to the fields of genetic sequencing and mutation screening.

Reference Sequence Constructs

Unlike prior art sequence alignment methods that use a single reference sequence to align and genotype nucleic acid reads, the invention uses a construct that can account for the variability in genetic sequences within a species, population, or even among different cells in a single organism. Representations of the genetic variation can be presented as directed acyclic graphs (DAGs) (discussed above) or row-column alignment matrices, and these constructs can be used with the alignment methods of the invention provided that the parameters of the alignment algorithms are set properly (discussed below).

In preferred embodiments of the invention, the construct is a directed acyclic graph (DAG), i.e., having a direction and having no cyclic paths. (That is, a sequence path cannot travel through a position on the reference construct more than once.) In the DAG, genetic variation in a sequence is represented as alternate nodes. The nodes can be a section of conserved sequence or a gene, or simply a nucleic acid. The different possible paths through the construct represent known genetic variation. A DAG may be constructed for an entire genome of an organism, or the DAG may be constructed only for a portion of the genome, e.g., a chromosome, or smaller segment of genetic information. In some embodiments, the DAG represents greater than 1000 nucleic acids, e.g., greater than 10,000 nucleic acids, e.g., greater than 100,000 nucleic acids, e.g., greater than 1,000,000 nucleic acids. A DAG may represent a species (e.g., *Homo sapiens*) or a selected population (e.g., women having breast cancer), or even smaller subpopulations, such as genetic variation among different tumor cells in the same individual.

Figure 2A:
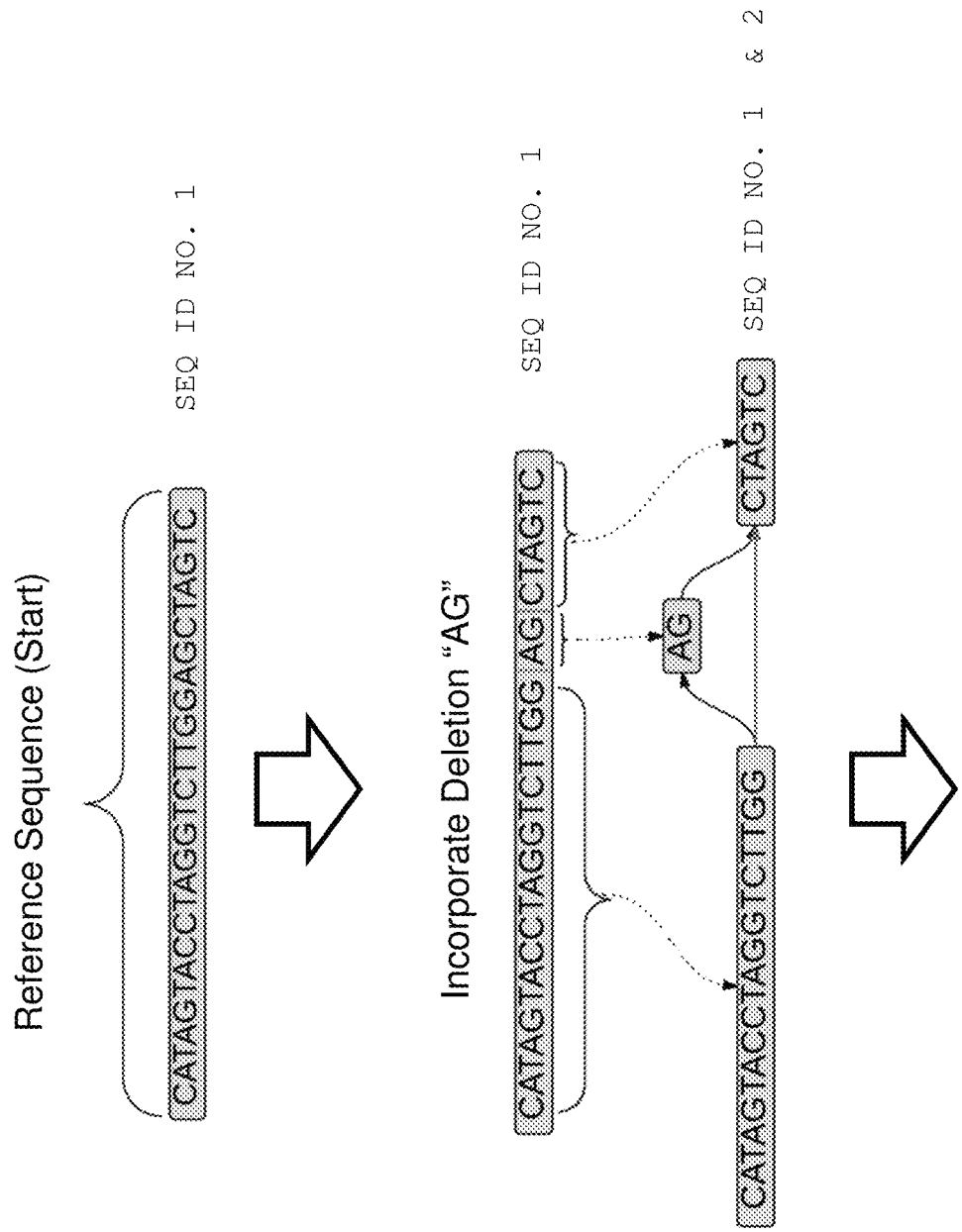
FIGS. 2A and 2B depict the construction of a directed acyclic graph (DAG) representing genetic variation in a reference sequence.
Figure 2B:
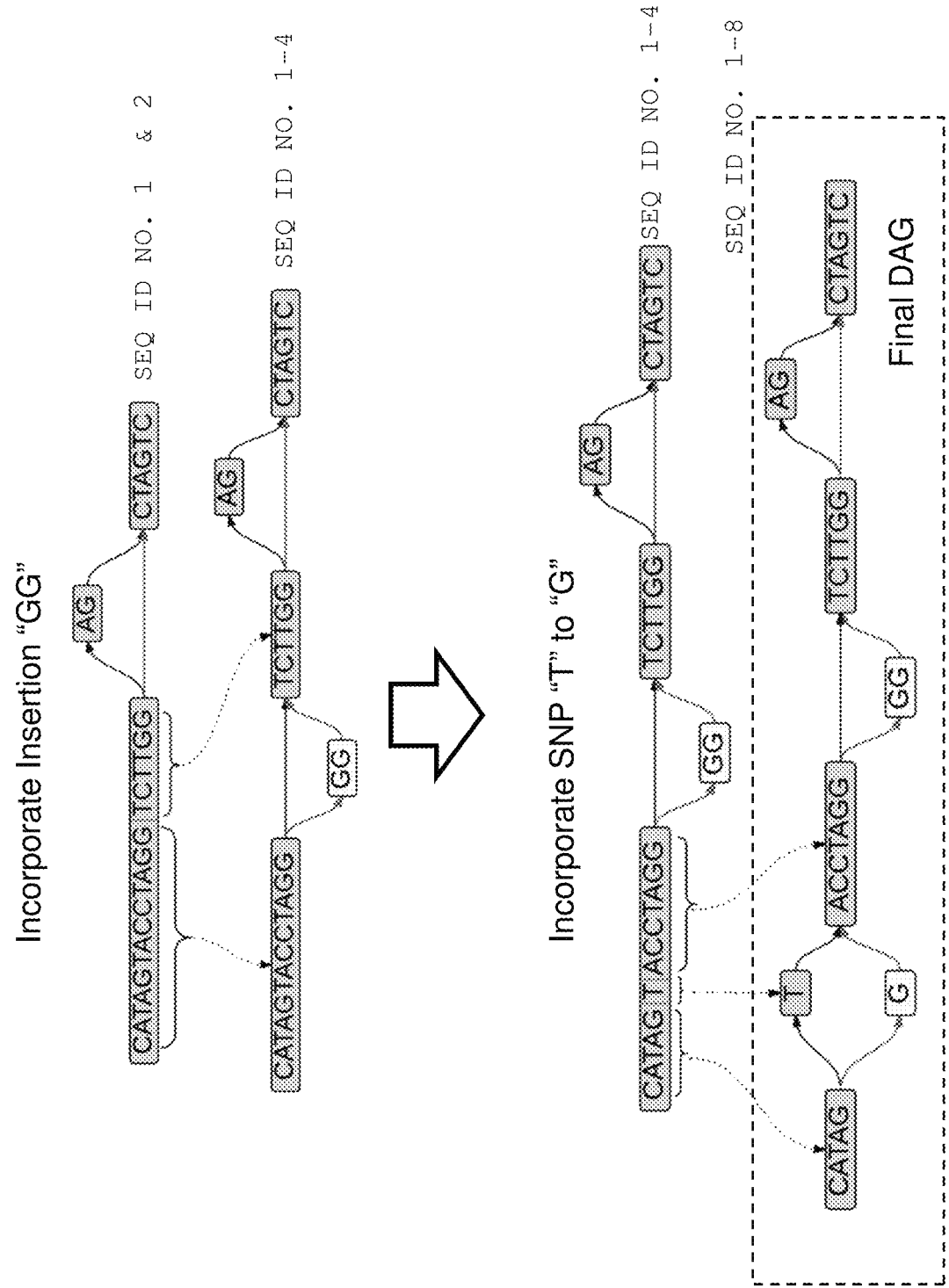

A simple example of DAG construction is shown in FIGS. 2A-B. As shown in FIG. 2A, the DAG begins with a reference sequence, shown in FIG. 2A as SEQ ID NO. 1: CATAGTACCTAGGTCTTGGAGCTAGTC. In practice, the reference sequence is often much longer, and may be an entire genome. In some embodiments, the sequence is a PASTA or FASTQ file. (FASTQ has become the default format for sequence data produced from next generation sequencers). In some embodiments, the reference sequence may be a standard reference, such as GRCh37. In some embodiment, the reference sequence is a sequence from non-diseased cells of a patient. As recognized by those of skill, each letter (or symbol) in the sequence actually corresponds to a nucleotide (e.g., a deoxyribonucleotide or a ribonucleotide) or an amino acid (e.g., histidine, leucine, lysine, etc.).

At the next step, a variant is added to the reference sequence, as shown in the bottom image of FIG. 2A. As shown in FIG. 2A the variant is the deletion of the sequence "AG" from the reference between the lines in the figure, i.e., SEQ ID NO. 2. Graphically, this deletion is represented by breaking the reference sequence into nodes before and after the deletion, and connecting the nodes with an edge and also creating a path from one node to the "AG" and then to the other node. Thus, one path between the nodes represents the reference sequence, while the other path represents the deletion.

In practice, the variants are called to the DAG by applying the entries in a variant call format (VCF) file, such as can be found at the 1000 Genomes Project website. Because each VCF file is keyed to a specific reference genome, it is not difficult to identify where the strings should be located. In fact, each entry in a VCF file can be thought of as combining with the reference to create separate graph, as displayed in FIG. 3. Note the VCF entries in FIGS. 2A-B do not correspond to the VCF entries of FIG. 3. It is also possible to identify variants for inclusion into the DAG by comparing the sequences of non-diseased and diseased cells of an individual.

Moving to FIG. 2B, a second VCF entry, corresponding to an insertion "GG" at a specific position is added to produce an expanded DAG, i.e., including SEQ ID NO. 3 and SEQ ID NO. 4. Next, a third VCF entry can be added to the expanded DAG to account for a SNP earlier in the reference sequence, i.e., including SEQ ID NOS. 5-8. Thus, in three steps, a DAG has been created against which nucleic acid reads can be aligned (as discussed below.)

In practice, the DAGs are represented in computer memory (hard disk, FLASH, cloud memory, etc.) as a set of nodes, S, wherein each node is defined by a string, a set of parent nodes, and a position. The string is the node's "content," i.e., sequence; the parent nodes define the node's position with respect to the other nodes in the graph; and the position of the node is relative to some canonical ordering in the system, e.g., the reference genome. While it is not strictly necessary to define the graph with respect to a reference sequence, it does make manipulation of the output data simpler. Of course, a further constraint on S is that it cannot include loops.

Figure 3:
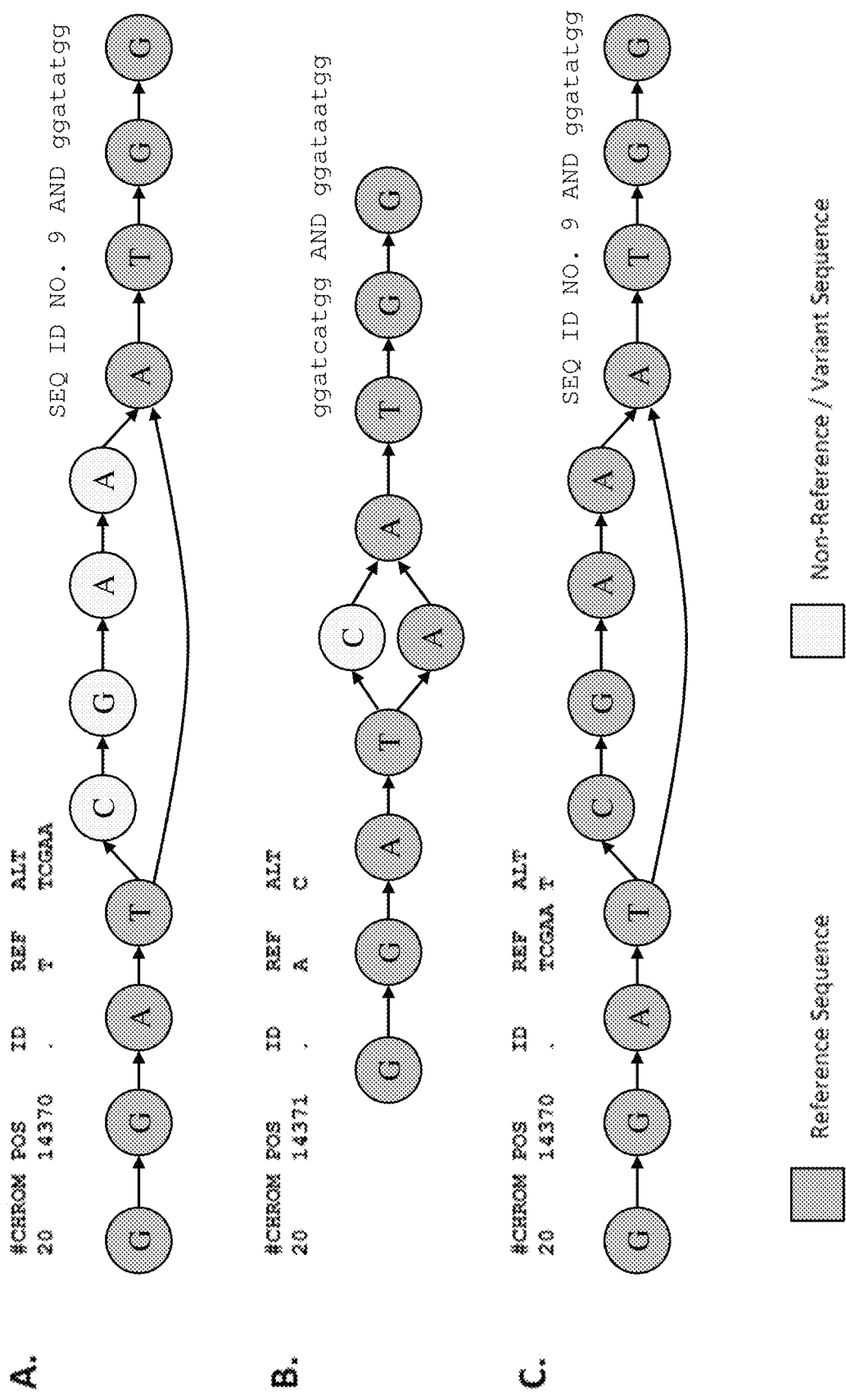
FIG. 3 depicts three variant call format (VCF) entries represented as directed acyclic graphs.

In many embodiments, the nodes comprise a plurality of characters, as shown in FIGS. 2A and 2B, however it is possible that a node may be a single character, e.g., representing a single base, as shown in FIG. 3. In instances where a node represents a string of characters, all of the characters in the node can be aligned with a single comparison step, rather than character-by-character calculations, as is done with conventional Smith-Waterman techniques. As a result, the computational burden is greatly reduced as compared to state-of-the-art methods. The reduced computational burden allows the alignment to be completed quicker, and with fewer resources. When used in next generation sequencing, where millions of small reads need to be aligned and assembled, this reduction in computational burden has tangible benefits in terms of reducing the cost of the alignment, while making meaningful information, i.e., genotype, available more quickly. In instances where a treatment will be tailored to a patient's genotype, the increased speed may allow a patient to begin treatment days earlier than using state-of-the-art methods.

Extrapolating this DAG method to larger structures, it is possible to construct DAGs that incorporate thousands of VCF entries representing the known variation in genetic sequences for a given region of a reference. Nonetheless, as a DAG becomes bulkier, the computations do take longer, and for many applications a smaller DAG is used that may only represent a portion of the sequence, e.g., a chromosome. In other embodiments, a DAG may be made smaller by reducing the size of the population that is covered by the DAG, for instance going from a DAG representing variation in breast cancer to a DAG representing variation in triple negative breast cancer. Alternatively, longer DAGs can be used that are customized based upon easily identified genetic markers that will typically result in a large portion of the DAG being consistent between samples. For example, aligning a set of nucleic acid reads from an African-ancestry female will be quicker against a DAG created with VCF entries from women of African ancestry as compared to a DAG accounting for all variations known in humans over the same sequence. It is to be recognized that the DAGs of the invention are dynamic constructs in that they can be modified over time to incorporate newly identified mutations. Additionally, algorithms in which the alignment results are recursively added to the DAG are also possible.

In the instance of string-to-DAG alignment, the gap penalties can be adjusted to make gap insertions even more costly, thus favoring an alignment to a sequence rather than opening a new gap in the overall sequence. Of course, with improvements in the DAG (discussed above) the incidence of gaps should decrease even further because mutations are accounted for in the DAG.

Alignment Algorithm

In one embodiment, an algorithm is used to align sequence reads against a directed acyclic graph (DAG). In contrast to the algorithm expressed in the Background, the alignment algorithm identifies the maximum value for $C_{i,j}$, by identifying the maximum score with respect to each sequence contained at a position on the DAG (e.g., the reference sequence construct). In fact, by looking "backwards" at the preceding positions, it is possible to identify the optimum alignment across a plurality of possible paths, The algorithm of the invention is carried out on a read (a.k.a. "string") and a directed acyclic graph (DAG), discussed above, For the purpose of defining the algorithm, let S be the string being aligned, and let D be the directed acyclic graph to which S is being aligned, The elements of the string, S, are bracketed with indices beginning at 1. Thus, if S is the string ATCGAA, S[1]=A, S[4]=G, etc.

For the DAG, each letter of the sequence of a node will be represented as a separate element, d, A predecessor of d is defined as:

(i) If d is not the first letter of the sequence of its node, the letter preceding d in its node is its (only) predecessor;

(ii) If d is the first letter of the sequence of its node, the last letter of the sequence of any node that is a parent of d's node is a predecessor of d.

The set of all predecessors is, in turn, represented as P[d].

In order to find the "best" alignment, the algorithm seeks the value of M[j,d], the score of the optimal alignment of the first j elements of S with the portion of the DAG preceding (and including) d. This step is similar to finding $H_{i,j}$ in equation 1 in the Background section. Specifically, determining M[j,d] involves finding the maximum of a, i, e, and 0, as defined below:

$$M[j,d]=\max\{a,i,e,0\} \quad (6)$$

where
e=max{M[j,p*]+DELETE_PENALTY} for p* in P[d]
i=M[j−1, d]+INSERT_PENALTY
a=max{M[j−1,p*]+MATCH_SCORE} for p* in P[d], if S[i]=d;
max{M[j−1,p*]+MISMATCH_PENALTY} for p* in P[d], if S[i]≠d As described above, e is the highest of the alignments of the first j characters of S with the portions of the DAG up to, but not including, d, plus an additional DELETE_PENALTY. Accordingly, if d is not the first letter of the sequence of the node, then there is only one predecessor, p, and the alignment score of the first j characters of S with the DAG (up-to-and-including p) is equivalent to M[j,p]+DELETE_PENALTY. In the instance where d is the first letter of the sequence of its node, there can be multiple possible predecessors, and because the DELETE_PENALTY is constant, maximizing [M[j,p]+DELETE_PENALTY] is the same as choosing the predecessor with the highest alignment score with the first j characters of S.

In equation (6), i is the alignment of the first j−1 characters of the string S with the DAG up-to-and-including d, plus an INSERT_PENALTY, which is similar to the definition of the insertion argument in SW (see equation 1).

Additionally, a is the highest of the alignments of the first j characters of S with the portions of the DAG up to, but not including d, plus either a MATCH_SCORE (if the jth character of S is the same as the character d) or a MISMATCH_PENALTY (if the jth character of S is not the same as the character d). As with e, this means that if d is not the first letter of the sequence of its node, then there is only one predecessor, i.e., p. That means a is the alignment score of the first j−1 characters of S with the DAG (up-to-and-including p), i.e., M[j−1,p], with either a MISMATCH_PENALTY or MATCH_SCORE added, depending upon whether d and the jth character of S match. In the instance where d is the first letter of the sequence of its node, there can be multiple possible predecessors. In this case, maximizing {M[j,p*]+MISMATCH_PENALTY or MATCH_SCORE} is the same as choosing the predecessor with the highest alignment score with the first j−1 characters of S (i.e., the highest of the candidate M[j−1,p*] arguments) and adding either a MISMATCH_PENALTY or a MATCH_SCORE depending on whether d and the jth character of S match.

Again, as in the SW algorithm discussed in the Background, the penalties, e.g., DELETE_PENALTY, INSERT_PENALTY, MATCH_SCORE and MISMATCH_PENALTY, can be adjusted to encourage alignment with fewer gaps, etc.

As described in the equations above, the algorithm finds the maximum value for each read by calculating not only the insertion, deletion, and match scores for that element, but looking backward (against the direction of the DAG) to any prior nodes on the DAG to find a maximum score. Thus, the algorithm is able to traverse the different paths through the DAG, which contain the known mutations. Because the graphs are directed, the backtracks, which move against the direction of the graph, follow the preferred variant sequence toward the origin of the graph, and the maximum alignment score identifies the most likely alignment within a high degree of certainty. While the equations above are represented as "maximum" values, "maximum" is intended to cover any form of optimization, including, for example, switching the signs on all of the equations and solving for a minimum value.

Figures 4A, 4B:
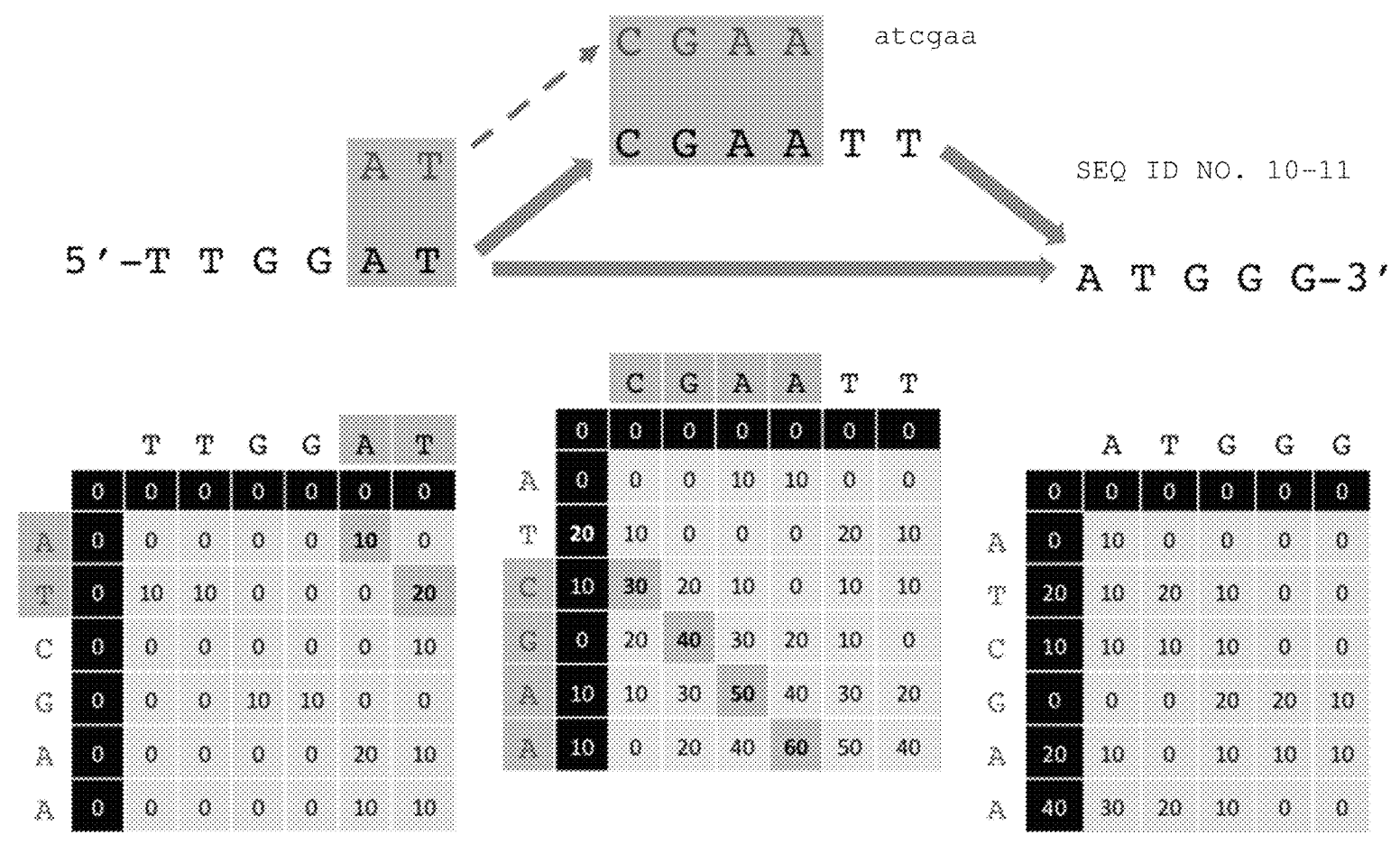

Implementation of the disclosed algorithm is exemplified in FIGS. 4A-B, where a sequence "ATCGAA" is aligned against a DAG that represents a reference sequence SEQ ID NO. 10: TTGGATATGGG and a known insertion event SEQ ID NO. 11: TTGGATCGAATTATGGG, where the insertion is underlined. FIG. 4A shows a pictorial representation of the read being compared to the DAG while FIG. 4B shows the actual matrices that correspond to the comparison. Like the Smith-Waterman technique discussed in the Background, the algorithm of the invention identifies the highest score and performs a backtrack to identify the proper location of the read. FIGS. 4A-B also highlight that the invention produces an actual match for the string against the construct, whereas the known methods (e.g., SW) would have been more likely to align the string to the wrong part of the reference, or reject the string as not generating a sufficiently-high alignment score to be included in the alignment. In the instances where the sequence reads include variants that were not included in the DAG, the aligned sequence will be reported out with a gap, insertion, etc.

Fabricating Constructs to Accommodate Disease Variability

Figure 5:
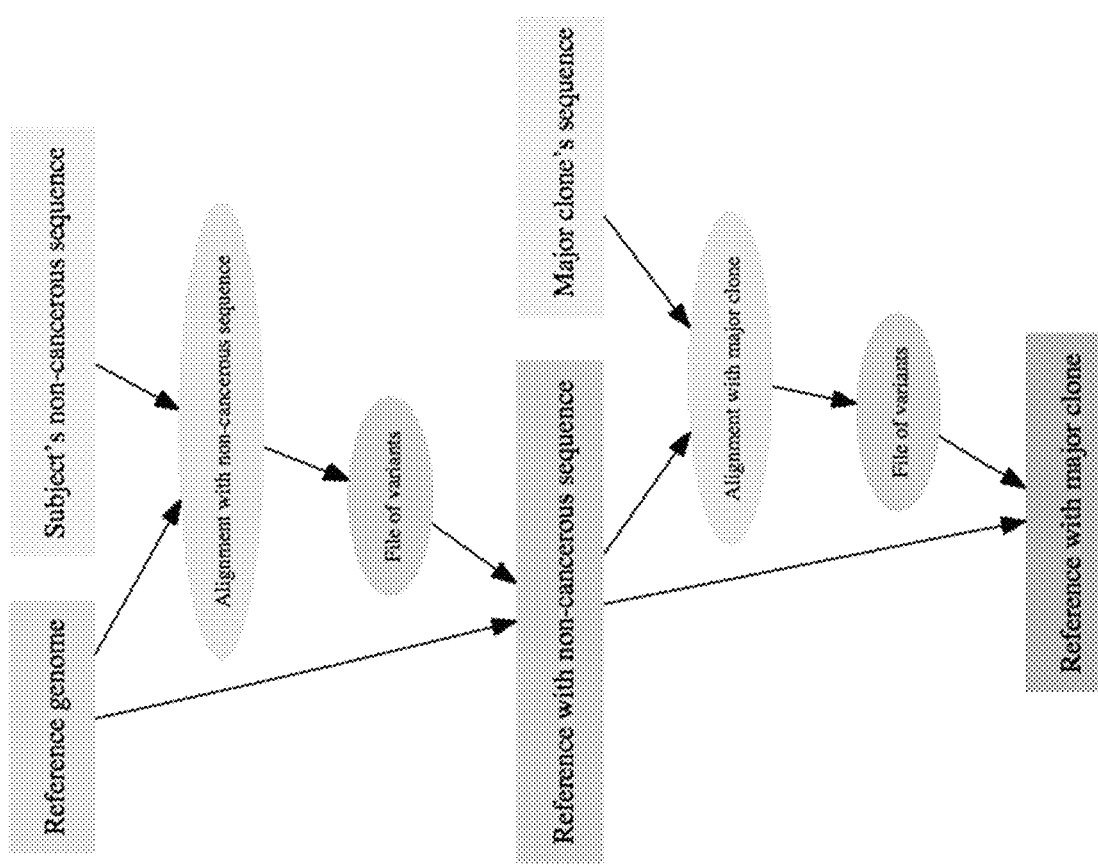
FIG. 5 depicts a workflow for producing a reference sequence construct that accounts for variations between the "normal" genome of a patient and an accepted reference in addition to variations between the "normal" genome of the patient and a genome of the patient corresponding to a diseased sample.

As mentioned above, the reference sequence construct can be prepared from existing variant files, or the construct can be prepared de novo, by comparing certain sampled sequences to a reference sequence. An example of such de novo construction is shown in FIG. 5. Starting with a reference genome, e.g., GRCh37, a non-cancerous sample is sequenced and compared to the reference to produce a file of variants. This file of variants is incorporated into a reference sequence construct, e.g., a DAG, as described above. The variants may include insertions, deletions, polymorphisms, structural variants, etc. The resulting construct can then be used to align reads from a diseased sample from the individual. This alignment step will provide immediate information about the location of "new" mutations that are likely correlated with a diseased state (i.e., the major clone), immediately differentiating them from mutations that already existed in the non-cancerous sample (because the latter are already included in the construct). Moreover, because the major clone sample is not aligned directly to the reference, but rather to a reference sequence construct, most of the major clone sample should align completely to the construct, and any unaligned reads will give immediate clues about the nature of the disease.

Figure 6:
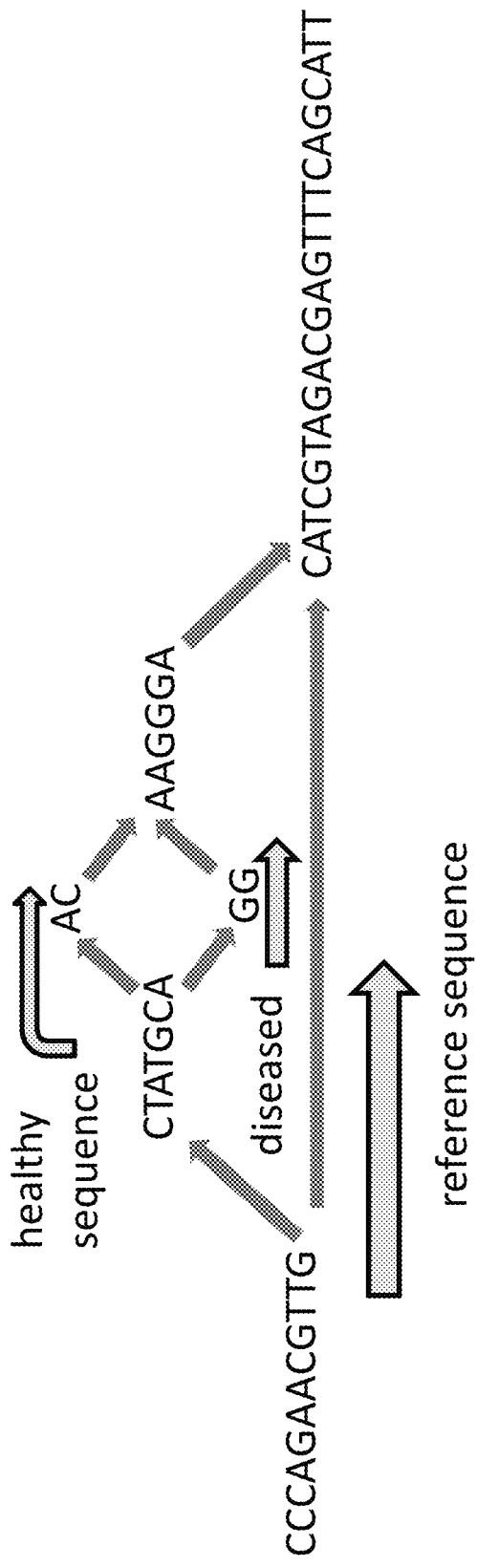
FIG. 6 illustrates a reference sequence construct based upon a reference sequence, a non-diseased sample that differs from the reference sequence by an insertion, and a diseased sample that differs from the non-diseased sample by a polymorphism associated with cancer.

Taking the example to the next level, the variants between the non-diseased and major clone sample can be incorporated into a new reference construct, "Reference with major clone" as shown in FIG. 5. Such a reference construct is shown in greater detail in FIG. 6. FIG. 6 uses three arbitrary sequences (SEQ ID NOS. 12-14) to illustrate the construction of the reference sequence and the incorporation of a reference, a non-diseased sequence, and a major clone. SEQ ID NO. 12 represents a portion of the reference sequence, which has been determined to be a good starting point. The individual in question, however, has a 15 bp insert that is not present in the reference sequence (SEQ ID NO. 13). Additionally, the individual, who has been identified as having cancer, has a sample of a tumor sequenced. Upon sequencing the tumor sample is found to have a polymorphism within the insert (SEQ ID NO. 14). As shown in the reference sequence construct at the bottom of FIG. 6, it is possible to account for all three sequences in this construct.

This construct in FIG. 6 is useful for at least two purposes. First, without any additional analysis, the reference sequence construct shows the relationship between the polymorphism and the major clone, separately from the insert, which arguably is not linked to the cancer. It should also be noted that the presence of a polymorphism within the insert would likely have been missed if SEQ ID NO. 14 was directly compared to SEQ ID NO. 12, as is typically done with contemporary cancer sequencing. Second, the reference sequence construct provides a new alignment tool against which new samples can be compared. For example a read (not shown) that aligns partially to the insert and includes the polymorphism is likely cancerous, whereas a read (not shown) that aligns partially to the insert, but contains "AC" instead of "GG" in the region of the polymorphism is likely not cancerous. Additionally, a new read that contained the polymorphism in addition to other mutations that did not align to the reference sequence construct suggests that the cancer may have progressed further and that greater testing, e.g., whole body MRI, may be in order.

Figure 7:
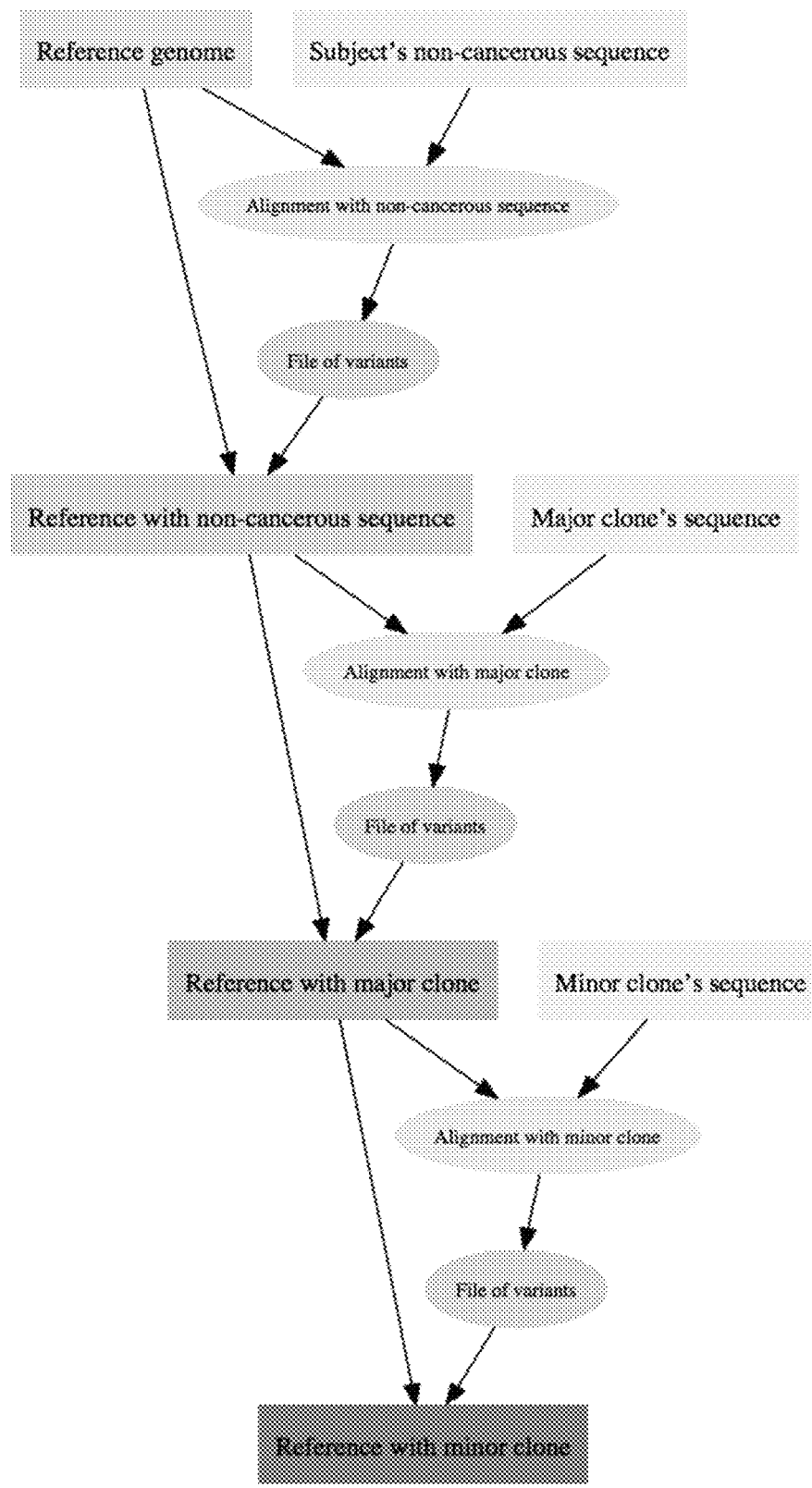
FIG. 7 depicts a workflow for producing a reference sequence construct that accounts for variations between the "normal" genome of a patient, a major cancerous clone, and a minor cancerous clone. The minor cancerous clone may result in metastatic disease.

The reference sequence construct shown in FIG. 6, may be improved iteratively, with the addition of more sequences, e.g., corresponding to identified minor clones, as shown in FIG. 7. In some cases the minor clones may represent metastatic cells or other progressed forms of the disease. Using the alignment algorithms described above, sequence reads corresponding to the minor clones can be aligned to the "Reference with the major clone" making clear where the mutations are located. Like the incorporation of the major clone mutation in FIG. 6, the minor clone mutations can also be incorporated into the reference sequence construct to create yet another new reference sequence construct "Reference with minor clone." Like "Reference with the major clone," "Reference with minor clone" can then provide information about the evolution of disease in the individual and be used to type new samples from the individual (or other individuals, as appropriate).

Figure 8:
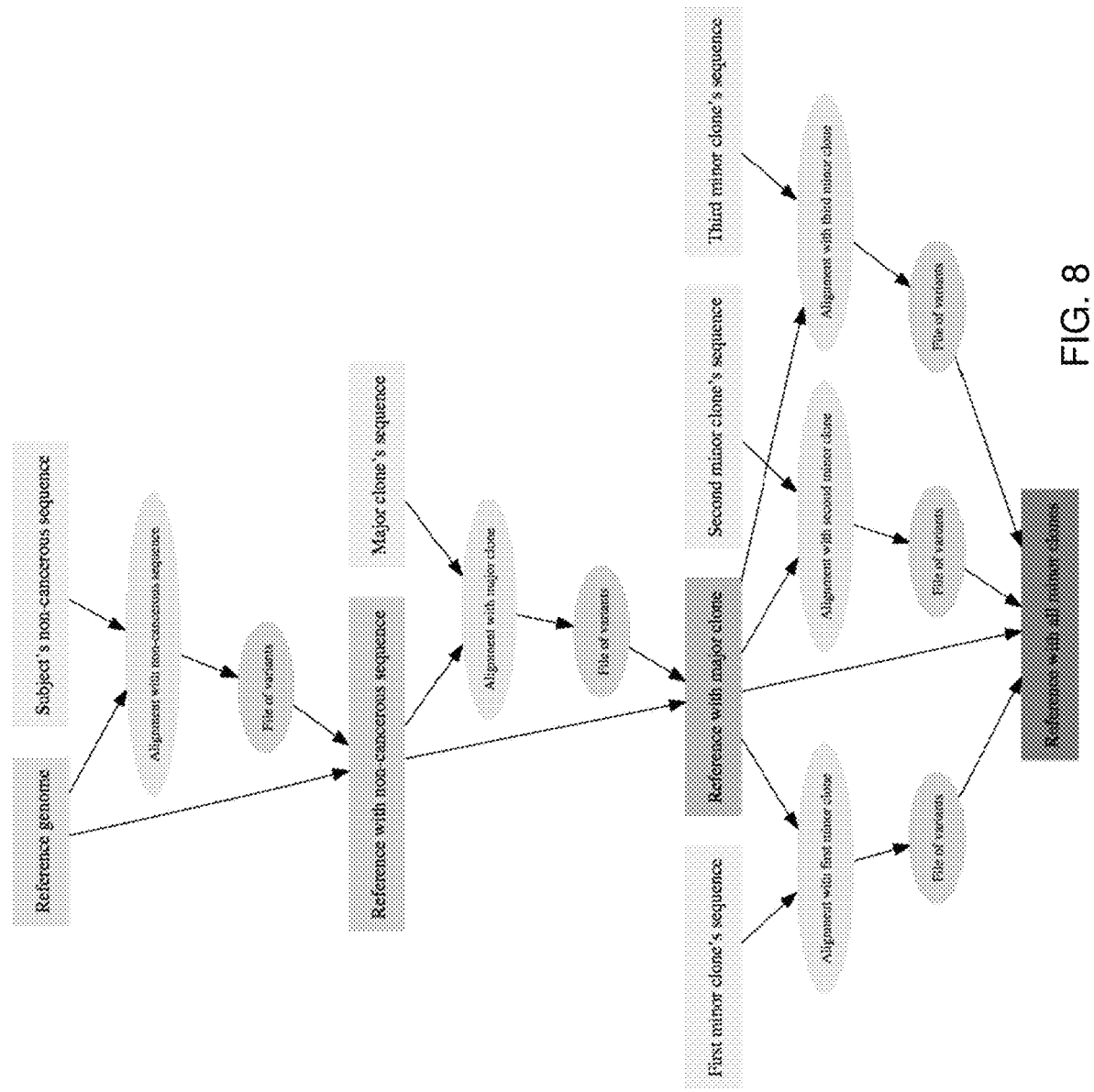
FIG. 8 depicts a workflow for producing a reference sequence construct that accounts for variations between the "normal" genome of a patient, a major cancerous clone, and several minor cancerous clones.
Figure 9:
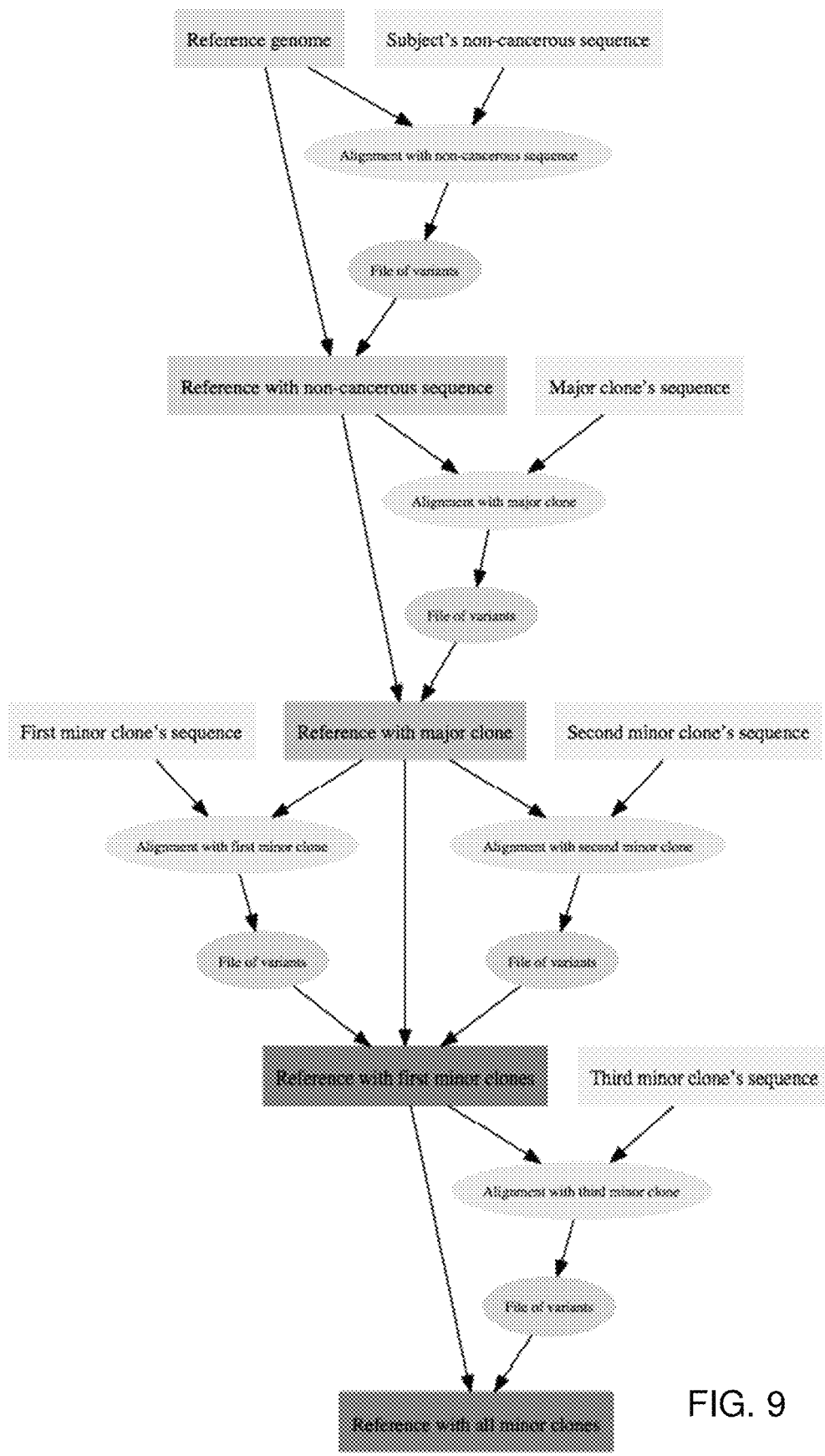
FIG. 9 depicts a workflow for producing a reference sequence construct that accounts for variations between the "normal" genome of a patient, a major cancerous clone, and several minor cancerous clones.

The process of aligning new samples to the reference sequence construct and then subsequently adding the newly-identified variants to the construct to create a new construct can be repeated indefinitely. In reality, because the reference sequence constructs are multivariate constructions stored on a non-transitory computer readable medium, the addition of new structures is trivial. Furthermore, the alignment of new reads to these highly complex reference constructs is computationally feasible and far less taxing than comparing new reads to each previous sequence individually. The process of aligning and improving on the constructs can be done in parallel, as shown in FIG. 8, or in series, as shown in FIG. 9. Whether the method is completed in parallel or in series, the resultant reference sequence construct should be identical. Nonetheless differing information about the evolution of the disease can be gleaned from the process depending upon the order in which new elements are added.

Opportunities For Parallelization

The sequential version of the Smith-Waterman-Gotoh algorithm has been adapted and significantly modified for massive parallelization. For example, an ASC model, called Smith-Waterman using *Associative Massive Parallelism* (SWAMP) is described in U.S. Patent Publication No. 2012/0239706, incorporated herein by reference in its entirety. Part of the parallelization for SWAMP (and other parallel processing systems) stems from the fact that the values along any anti-diagonal are independent of each other. Thus, all of the cells along a given anti-diagonal can be done in parallel to distribute the computational resources. The data dependencies shown in the above recursive equations limit the level of achievable parallelism but using a wavefront approach will still speed up this useful algorithm. A wavefront approach implemented by Wozniak (*Comput Appl in the Biosciences* (*CABIOS*), 13(2):145-150, 1997) on the Sun Ultra SPARC uses specialized SIMD-like video instructions. Wozniak used the SIMD registers to store the values parallel to the minor diagonal, reporting a two-fold speedup over a traditional implementation on the same machine. Following Wozniak's example, a similar way to parallelize code is to use the Streaming SIMD Extension (SSE) set for the ×86 architecture.

Designed by Intel, the vector-like operations complete a single operation/instruction on a small number of values (usually four, eight or sixteen) at a time. Many AMO and Intel chips support the various versions of SSE, and Intel has continued developing this technology with the Advanced Vector Extensions (AVX) for their modern chipsets.

In other implementations, Rognes and Seeberg (*Bioinformatics* (*Oxford, England*), 16(8):699-706, 2000) use the Intel Pentium processor with SSE's predecessor, MMX SIMD instructions for their implementation. The approach that developed out of the work of Rognes and Seeberg (*Bioinformatics*, 16(8):699-706, 2000) for ParAlign does not use the wavefront approach (Rognes, *Nuc Acids Res*, 29(7):1647-52, 2001; Saebo et al., *Nuc Acids Res*, 33(suppl 2):W535-W539, 2005). Instead, they align the SIMD registers parallel to the query sequence, computing eight values at a time, using a pre-computed query-specific score matrix. Additional details of this method can be found in U.S. Pat. No. 7,917,302, incorporated by reference herein. The way Rognes and Seeberg layout the SIMD registers, the north neighbor dependency could remove up to one third of the potential speedup gained from the SSE parallel "vector" calculations. To overcome this, they incorporate SWAT-like optimizations. With large affine gap penalties, the northern neighbor will be zero most of the time. If this is true, the program can skip computing the value of the north neighbor, referred to as the "lazy F evaluation" by Farrar (*Bioinformatics*, 23(2):156-161, 2007). Rognes and Seeberg are able to reduce the number of calculations of Equation 1 to speed up their algorithm by skipping it when it is below a certain threshold. A six-fold speedup was reported in (Rognes and Seeberg, *Bioinformatics*, 16(8):699-706, 2000) using 8-way vectors via the MMX/SSE instructions and the SWAT-like extensions.

In the SSE work done by Farrar (*Bioinformatics*, 23(2):156-161, 2007), a striped or strided pattern of access is used to line up the SIMD registers parallel to the query registers. Doing so avoids any overlapping dependencies. Again incorporating the SWAT-like optimizations (Farrar, *Bioinformatics* 23(2):156-161, 2007) achieves a 2-8 time speedup over Wozniak (*CABIOS* 13(2):145-150, 1997) and Rognes and Seeberg (*Bioinformatics* (Oxford, England), 16(8):699-706, 2000) SIMD implementations. The block substitution matrices and efficient and clever inner loop with the northern (F) conditional moved outside of that inner loop are important optimizations. The strided memory pattern access of the sixteen, 8-bit elements for processing improves the memory access time as well, contributing to the overall speedup.

Farrar (*Sequence Analysis,* 2008) extended his work for a Cell Processor manufactured by Sony, Toshiba and IBM. This Cell Processor has one main core and eight minor cores. The Cell Broadband Engine was the development platform for several more Smith-Waterman implementations including SWPS3 by Szatkowski, et. al (*BMC Res Notes* 1(107), 2008) and CBESW by Wirawan, et. al (*BMC Bioinformatics* 9 (377) 2008) both using Farrar's striping approach. Rudnicki, et. al. (*Fund Inform.* 96, 181-194, 2009) used the PS3 to develop a method that used parallelization over multiple databases sequences.

Rognes (*BMC Bioinformatics* 12 (221), 2011) also developed a multi-threaded approach called SWIPE that processes multiple database sequences in parallel. The focus was to use a SIMD approach on "ordinary CPUs." This investigation using coarse-grained parallelism split the work using multiple database sequences in parallel is similar to the graphics processor units (GPU)-based tools described in the CUDASW by Liu, et al. (*BMC Res Notes* 2(73), 2009) and Ligowski and Rudnicki (*Eight Annual International Workshop on High Peformance Computational Biology,* Rome, 2009). There have been other implementations of GPU work with CUDASW++2.0 by Liu, et. al. (*BMC Res Notes* 3(93), 2010) and Ligowski, et. al (*GPU Computing Gems, Emerald Edition*, Morgan Kaufmann, 155-157, 2011).

In other variations, small-scale vector parallelization (8, 16 or 32-way parallelism) can be used to make the calculations accessible via GPU implementations that align multiple sequences in parallel. The theoretical peak speedup for the calculations is a factor of m, which is optimal. A 96-fold speedup for the ClearSpeed implementation using 96 processing elements, confirming the theoretical speedup.

Parallel Computing Models

The main parallel model used to develop and extend Smith-Waterman sequence alignment is the ASsociative Computing (ASC) (Potter et al., *Computer,* 27(11):19-25, 1994). Efficient parallel versions of the Smith-Waterman algorithm are described herein. This model and one other model are described in detail in this section.

Some relevant vocabulary is defined here. Two terms of interest from Flynn's Taxonomy of computer architectures are MIMD and SIMD, two different models of parallel computing. A cluster of computers, classified as a multiple-instruction, multiple-data (MIMD) model is used as a proof-of-concept to overcome memory limitations in extremely large-scale alignments. Section 8 describes usage of the MIMD model. An extended data-parallel, single-instruction multiple-data (SIMD) model known as ASC is also described.

Multiple Instruction, Multiple Data (MIMD)

The multiple-data, multiple-instruction model or MIMD model describes the majority of parallel systems currently available, and include the currently popular cluster of computers. The MIMD processors have a full-fledged central processing unit (CPU), each with its own local memory (Quinn, *Parallel Computing: Theory and Practice,* 2nd ed., New York: McGraw-Hill, 1994). In contrast to the SIMD model, each of the MIMD processors stores and executes its own program asynchronously. The MIMD processors are connected via a network that allows them to communicate but the network used can vary widely, ranging from an Ethernet, Myrinet, and InfiniBand connection between machines (cluster nodes). The communications tend to employ a much looser communications structure than SIMDs, going outside of a single unit. The data is moved along the network asynchronously by individual processors under the control of their individual program they are executing. Typically, communication is handled by one of several different parallel languages that support message-passing. A very common library for this is known as the Message Passing Interface (MPI). Communication in a "SIMD-like" fashion is possible, but the data movements will be asynchronous. Parallel computations by MIMDs usually require extensive communication and frequent synchronizations unless the various tasks being executed by the processors are highly independent (i.e. the so-called "embarrassingly parallel" or "pleasingly parallel" problems). The work presented in Section 8 uses an AMD Opteron cluster connected via InfiniBand.

Unlike SIMDs, the worst-case time required for the message-passing is difficult or impossible to predict. Typically, the message-passing execution time for MIMD software is determined using the average case estimates, which are often determined by trial, rather than by a worst case theoretical evaluation, which is typical for SIMDs. Since the worst case for MIMD software is often very bad and rarely occurs, average case estimates are much more useful. As a result, the communication time required for a MIMD on a particular problem can be and is usually significantly higher than for a SIMD. This leads to the important goal in MIMD programming (especially when message-passing is used) to minimize the number of inter-processor communications required and to maximize the amount of time between processor communications. This is true even at a single card acceleration level, such as using graphics processors or GPUs.

Data-parallel programming is also an important technique for MIMD programming, but here all the tasks perform the same operation on different data and are only synchronized at various critical points. The majority of algorithms for MIMD systems are written in the Single-Program, Multiple-Data (SPMD) programming paradigm. Each processor has its own copy of the same program, executing the sections of the code specific to that processor or core on its local data. The popularity of the SPMD paradigm stems from the fact that it is quite difficult to write a large number of different programs that will be executed concurrently across different processors and still be able to cooperate on solving a single problem. Another approach used for memory-intensive but not compute-intensive problems is to create a virtual memory server, as is done with JumboMem, using the work presented in Section 8. This uses MPI in its underlying implementation.

Single Instruction, Multiple Data (SIMD)

The SIMD model consists of multiple, simple arithmetic processing elements called PEs. Each PE has its own local memory that it can fetch and store from, but it does not have the ability to compile or execute a program. As used herein, the term "parallel memory" refers to the local memories, collectively, in a computing system. For example, a parallel memory can be the collective of local memories in a SIMD computer system (e.g., the local memories of PEs), the collective of local memories of the processors in a MIMD computer system (e.g., the local memories of the central processing units) and the like. The compilation and execution of programs are handled by a processor called a control unit (or front end) (Quinn, *Parallel Computing: Theory and Practice,* 2nd ed., New York: McGraw-Hill, 1994). The control unit is connected to all PEs, usually by a bus.

All active PEs execute the program instructions received from the control unit synchronously in lockstep. "In any time unit, a single operation is in the same state of execution on multiple processing units, each manipulating different data" (Quinn, *Parallel Computing: Theory and Practice,* 2nd ed., New York: McGraw-Hill, 1994), at page 79. While the same instruction is executed at the same time in parallel by all active PEs, some PEs may be allowed to skip any particular instruction (Baker, SIMD and MASC: Course notes from CS 6/73301: Parallel and Distributed Computing-power point slides, (2004) 2004). This is usually accomplished using an "if-else" branch structure where some of the PEs execute the if instructions and the remaining PEs execute the else part. This model is ideal for problems that are "data-parallel" in nature that have at most a small number of if-else branching structures that can occur simultaneously, such as image processing and matrix operations.

Data can be broadcast to all active PEs by the control unit and the control unit can also obtain data values from a particular PE using the connection (usually a bus) between the control unit and the PEs. Additionally, the set of PE are connected by an interconnection network, such as a linear array, 2-D mesh, or hypercube that provides parallel data movement between the PEs. Data is moved through this network in synchronous parallel fashion by the PEs, which execute the instructions including data movement, in lockstep. It is the control unit that broadcasts the instructions to the PEs. In particular, the SIMD network does not use the message-passing paradigm used by most parallel computers today. An important advantage of this is that SIMD network communication is extremely efficient and the maximum time required for the communication can be determined by the worst-case time of the algorithm controlling that particular communication.

The remainder of this section is devoted to describing the extended SIMD ASC model. ASC is at the center of the algorithm design and development for this discussion.

Associative Computing Model

The ASsocative Computing (ASC) model is an extended SIMD based on the STARAN associative SIMD computer, designed by Dr. Kenneth Batcher at Goodyear Aerospace and its heavily Navy-utilized successor, the ASPRO.

Developed within the Department of Computer Science at Kent State University, ASC is an algorithmic model for associative computing (Potter et al., Computer, 27(11):19-25, 1994) (Potter, *Associative Computing: A Programming Paradigm for Massively Parallel Computers,* Plenum Publishing, 1992). The ASC model grew out of work on the STARAN and MPP, associative processors built by Goodyear Aerospace. Although it is not currently supported in hardware, current research efforts are being made to both efficiently simulate and design a computer for this model.

As an extended SIMD model, ASC uses synchronous data-parallel programming, avoiding both multi-tasking and asynchronous point-to-point communication routing. Multi-tasking is unnecessary since only one task is executed at any time, with multiple instances of this task executed in lockstep on all active processing elements (PEs). ASC, like SIMD programmers, avoid problems involving load balancing, synchronization, and dynamic task scheduling, issues that must be explicitly handled in MPI and other MIMD cluster paradigms.

Figure 10:
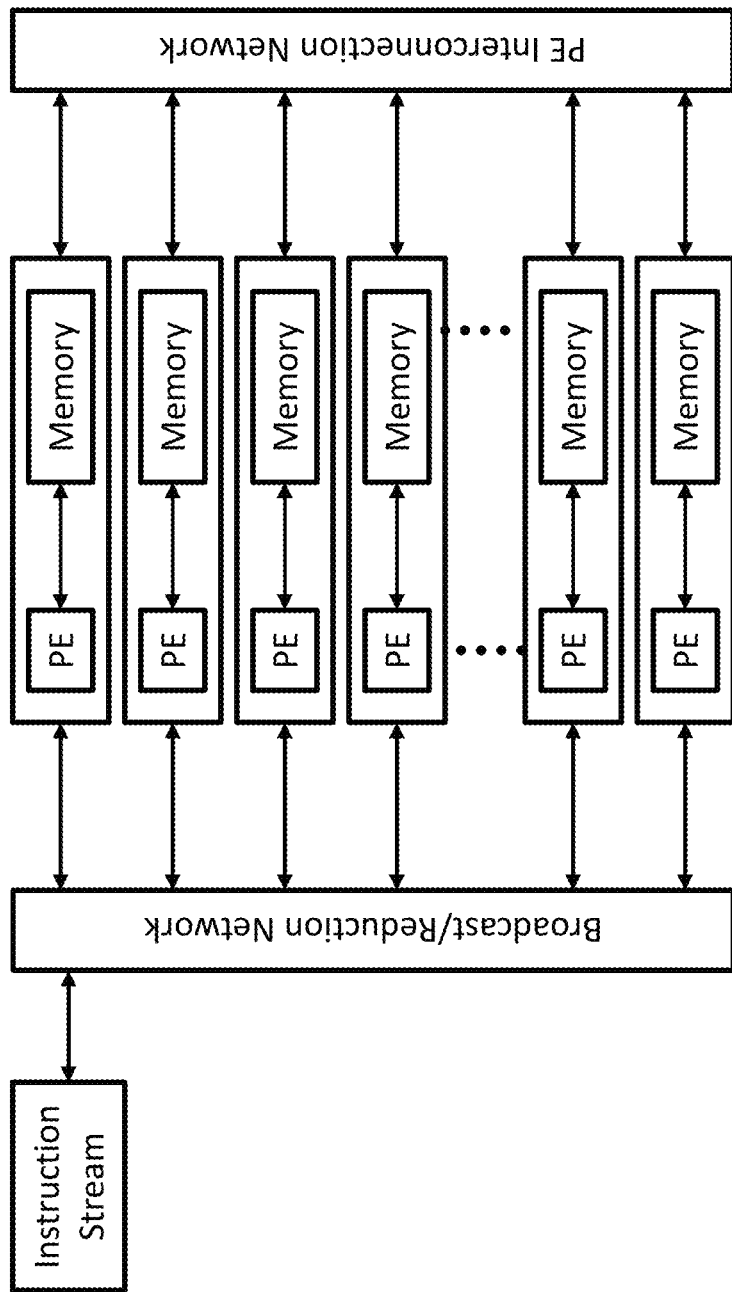
FIG. 10 depicts an associative computing model for parallel processing.

FIG. 10 shows a conceptual model of an ASC computer. There is a single control unit, also known as an instruction stream (IS), and multiple processing elements (PEs), each with its own local memory. The control unit and PE array are connected through a broadcast/reduction network and the PEs are connected together through a PE data interconnection network.

As seen in FIG. 10, a PE has access to data located in its own local memory. The data remains in place and responding (active) PEs process their local data in parallel. The reference to the word associative is related to the use of searching to locate data by content rather than memory addresses. The ASC model does not employ associative memory, instead it is an associative processor where the general cycle is to search-process-retrieve. An overview of the model is available in (Potter et al., *Computer*, 27(11): 19-25, 1994).

The tabular nature of the algorithm lends itself to computation using ASC due to the natural tabular structure of ASC data structures. Highly efficient communication across the PE interconnection network for the lockstep shifting of data of the north and northwest neighbors, and the fast constant time associative functions for searching and for maximums across the parallel computations are well utilized by SWAMP.

The associative operations are executed in constant time (Jin et al., 15*th International Parallel and Distributed Processing Symposium (IPDPS'01)* Workshops, San Francisco, p. 193, 2001), due to additional hardware required by the ASC model. These operations can be performed efficiently (but less rapidly) by any SIMD-like machine, and has been successfully adapted to run efficiently on several SIMD hardware platforms (Yuan et al., *Parallel and Distributed Computing Systems (PDCS)*, Cambridge, Mass., 2009; Trahan et al., *J. of Parallel and Distributed Computing (JPDC)*, 2009). SWAMP and other ASC algorithms can therefore be efficiently implemented on other systems that are closely related to SIMDs including vector machines, which is why the model is used as a paradigm.

The control unit fetches and decodes program instructions and broadcasts control signals to the PEs. The PEs, under the direction of the control unit, execute these instructions using their own local data. All PEs execute instructions in a lockstep manner, with an implicit synchronization between instructions. ASC has several relevant high-speed global operations: associative search, maximum/minimum search, and responder selection/detection. These are described in the following section.

Associative Functions

The functions relevant to the SWAMP algorithms are discussed below.

Associative Search

The basic operation in an ASC algorithm is the associative search. An associative search simultaneously locates the PEs whose local data matches a given search key. Those PEs that have matching data are called responders and those with non-matching data are called non-responders. After performing a search, the algorithm can then restrict further processing to only affect the responders by disabling the non-responders (or vice versa). Performing additional searches may further refine the set of responders. Associative search is heavily utilized by SWAMP+ in selecting which PEs are active within a parallel act within a diagonal.

Maximum/Minimum Search

In addition to simple searches, where each PE compares its local data against a search key using a standard comparison operator (equal, less than, etc.), an associative computer can also perform global searches, where data from the entire PE array is combined together to determine the set of responders. The most common type of global search is the maximum/minimum search, where the responders are those PEs whose data is the maximum or minimum value across the entire PE array. The maximum value is used by SWAMP+ in every diagonal it processes to track the highest value calculated so far. Use of the maximum search occurs frequently, once in a logical parallel act, m+n times per alignment.

Responder Selection/Detection

An associative search can result in multiple responders and an associative algorithm can process those responders in one of three different modes: parallel, sequential, or single selection. Parallel responder processing performs the same set of operations on each responder simultaneously. Sequential responder processing selects each responder individually, allowing a different set of operations for each responder. Single responder selection (also known as pickOne) selects one, arbitrarily chosen, responder to undergo processing. In addition to multiple responders, it is also possible for an associative search to result in no responders. To handle this case, the ASC model can detect whether there were any responders to a search and perform a separate set of actions in that case (known as anyResponders). In SWAMP, multiple responders that contain characters to be aligned are selected and processed in parallel, based on the associative searches mentioned above. Single responder selection occurs if and when there are multiple values that have the exact same maximum value when using the maximum/minimum search.

PE Interconnection Network

Most associative processors include some type of PE interconnection network to allow parallel data movement within the array. The ASC model itself does not specify any particular interconnection network and, in fact, many useful associative algorithms do not require one.

Typically associative processors implement simple networks such as 1D linear arrays or 2D meshes. These networks are simple to implement and allow data to be transferred quickly in a synchronous manner. The 1D linear array is sufficient for the explicit communication between PEs in the SWAMP algorithms, for example.

Parallel Computing Systems

Figure 11:
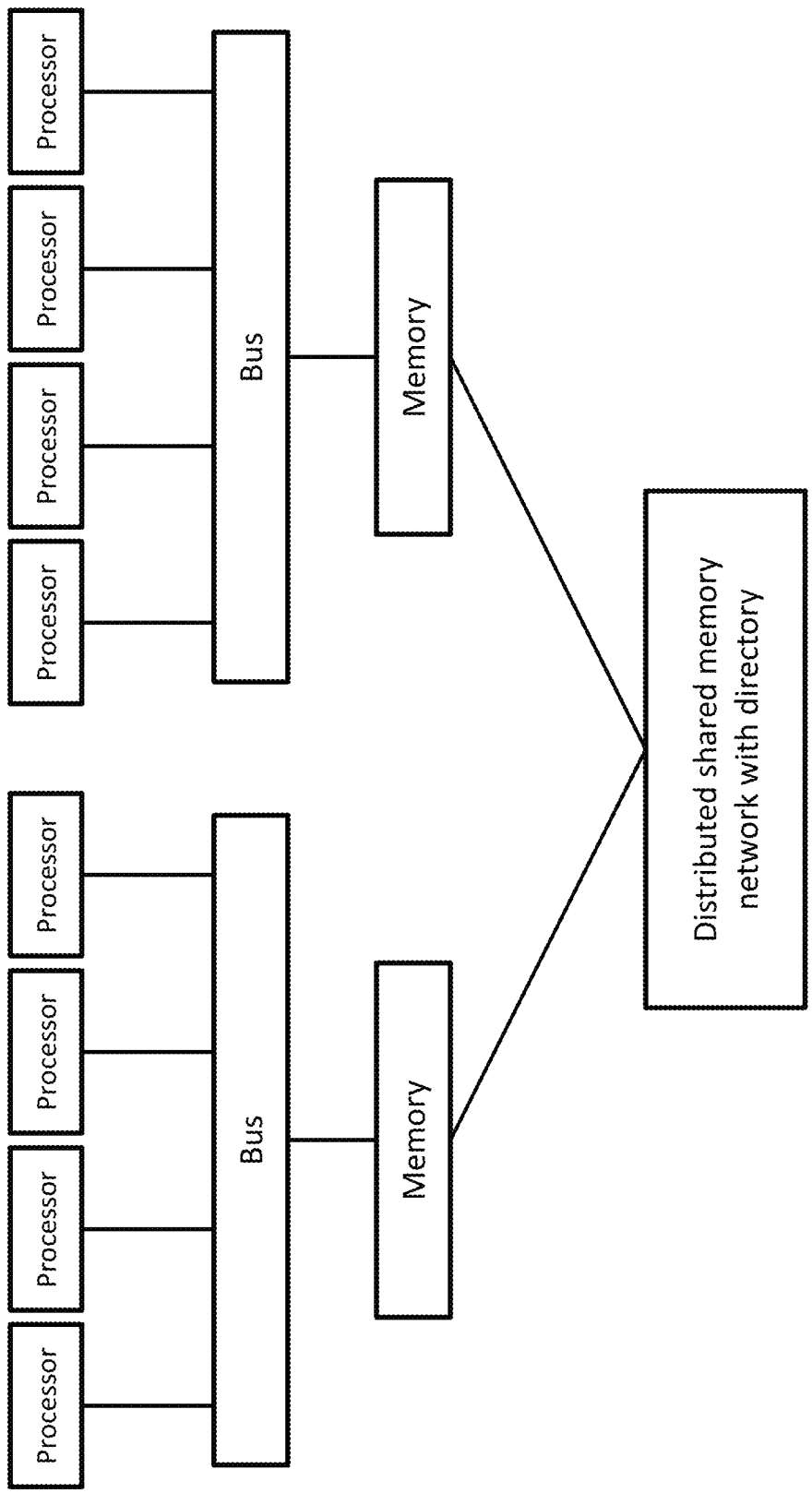
FIG. 11 depicts an architecture for parallel computation.

A generalized parallel processing architecture is shown in FIG. 11. While each component is shown as having a direct connection, it is to be understood that the various elements may be geographically separated but connected via a network, e.g., the internet. While hybrid configurations are possible, the main memory in a parallel computer is typically either shared between all processing elements in a single address space, or distributed, i.e., each processing element has its own local address space. (Distributed memory refers to the fact that the memory is logically distributed, but often implies that it is physically distributed as well.) Distributed shared memory and memory virtualization combine the two approaches, where the processing element has its own local memory and access to the memory on non-local processors. Accesses to local memory are typically faster than accesses to non-local memory.

Computer architectures in which each element of main memory can be accessed with equal latency and bandwidth are known as Uniform Memory Access (OMA) systems, Typically, that can be achieved only by a shared memory system, in which the memory is not physically distributed. A system that does not have this property is known as a Non-Uniform Memory Access (NUMA) architecture. Distributed memory systems have non-uniform memory access.

Processor-processor and processor-memory communication can be implemented in hardware in several ways, including via shared (either multiported or multiplexed) memory, a crossbar switch, a shared bus or an interconnect network of a myriad of topologies including star, ring, tree, hypercube, fat hypercube (a hypercube with more than one processor at a node), or n-dimensional mesh.

Parallel computers based on interconnected networks must incorporate routing to enable the passing of messages between nodes that are not directly connected. The medium used for communication between the processors is likely to be hierarchical in large multiprocessor machines. Such resources are commercially available for purchase for dedicated use, or these resources can be accessed via "the cloud," e.g., Amazon Cloud Computing.

A computer generally includes a processor coupled to a memory via a bus. Memory can include RAM or ROM and preferably includes at least one tangible, non-transitory medium storing instructions executable to cause the system to perform functions described herein. As one skilled in the art would recognize as necessary or best-suited for performance of the methods of the invention, systems of the invention include one or more processors (e.g., a central processing unit (CPU), a graphics processing unit (GPU), etc.), computer-readable storage devices (e.g., main memory, static memory, etc.), or combinations thereof which communicate with each other via a bus.

A processor may be any suitable processor known in the art, such as the processor sold under the trademark XEON E7 by Intel (Santa Clara, Calif.) or the processor sold under the trademark OPTERON 6200 by AMD (Sunnyvale, Calif.).

Memory may refer to a computer-readable storage device and can include any machine-readable medium on which is stored one or more sets of instructions (e.g., software embodying any methodology or function found herein), data (e.g., embodying any tangible physical objects such as the genetic sequences found in a patient's chromosomes), or both. While the computer-readable storage device can in an exemplary embodiment be a single medium, the term "computer-readable storage device" should be taken to include a single medium or multiple media (e.g., a centralized or distributed database, and/or associated caches and servers) that store the one or more sets of instructions or data. The term "computer-readable storage device" shall accordingly be taken to include, without limit, solid-state memories (e.g., subscriber identity module (SIM) card, secure digital card (SD card), micro SD card, or solid-state drive (SSD)), optical and magnetic media, and any other tangible storage media. Preferably, a computer-readable storage device includes a tangible, non-transitory medium. Such non-transitory media excludes, for example, transitory waves and signals. "Non-transitory memory" should be interpreted to exclude computer readable transmission media, such as signals, per se.

Input/output devices according to the invention may include a video display unit (e.g., a liquid crystal display (LCD) or a cathode ray tube (CRT) monitor), an alphanumeric input device (e.g., a keyboard), a cursor control device (e.g., a mouse or trackpad), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Sample Acquisition and Preparation

The invention includes methods for producing sequences (e.g., nucleic acid sequences, amino acid sequences) corresponding to nucleic acids recovered from biological samples. In some embodiments the resulting information can be used to identify mutations present in nucleic acid material obtained from a subject. In some embodiments, a sample, i.e., nucleic acids (e.g. DNA or RNA) are obtained from a subject, the nucleic acids are processed (lysed, amplified, and/or purified) and the nucleic acids are sequenced using a method described below. In many embodiments, the result of the sequencing is not a linear nucleic acid sequence, but a collection of thousands or millions of individual short nucleic acid reads that must be re-assembled into a sequence for the subject. Once the reads are aligned to produce a sequence, the aligned sequence can be compared to reference sequences to identify mutations that may be indicative of disease, for example. In other embodiments, the subject may be identified with particular mutations based upon the alignment of the reads against a reference sequence construct, i.e., a directed acyclic graph ("DAG") as described above.

For any of the above purposes, methods may be applied to biological samples. The biological samples may, for example, comprise samples of blood, whole blood, blood plasma, tears, nipple aspirate, serum, stool, urine, saliva, circulating cells, tissue, biopsy samples, hair follicle or other samples containing biological material of the patient. One issue in conducting tests based on such samples is that, in most cases only a tiny amount of DNA or RNA containing a mutation of interest may be present in a sample. This is especially true in non-invasive samples, such as a buccal swab or a blood sample, where the mutant nucleic acids are present in very small amounts. In some embodiments, the nucleic acid fragments may be naturally short, that is, random shearing of relevant nucleic acids in the sample can generate short fragments. In other embodiments, the nucleic acids are purposely fragmented for ease of processing or because the sequencing techniques can only sequence reads of less than 1000 bases, e.g., less than 500 bases, e.g., less than 200 bases, e.g., less than 100 bases, e.g., less than 50 bases. While the methods described herein can be used to align sequences of varying length, in some embodiments, the majority of the plurality of nucleic acid reads will follow from the sequencing method and comprise less than 1000 bases, e.g., less than 500 bases, e.g., less than 200 bases, e.g., less than 100 bases, e.g., less than 50 bases.

Nucleic acids may be obtained by methods known in the art. Generally, nucleic acids can be extracted from a biological sample by a variety of techniques such as those described by Maniatis, et al., Molecular Cloning: A Laboratory Manual, Cold Spring Harbor, N.Y., pp. 280-281, (1982), the contents of which is incorporated by reference herein in its entirety.

It may be necessary to first prepare an extract of the sample and then perform further steps—i.e., differential precipitation, column chromatography, extraction with organic solvents and the like—in order to obtain a sufficiently pure preparation of nucleic acid. Extracts may be prepared using standard techniques in the art, for example, by chemical or mechanical lysis of the cell. Extracts then may be further treated, for example, by filtration and/or centrifugation and/or with chaotropic salts such as guanidinium isothiocyanate or urea or with organic solvents such as phenol and/or $HCCl_3$ to denature any contaminating and potentially interfering proteins. In some embodiments, the sample may comprise RNA, e.g., mRNA, collected from a subject sample, e.g., a blood sample. General methods for RNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., BioTechniques 18:42044 (1995). The contents of each of these references is incorporated by reference herein in their entirety. In particular, RNA isolation can be performed using a purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MASTERPURE Complete DNA and RNA Purification Kit (EPICENTRE, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

Analytical Sequencing

Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes. Prior to sequencing it may be additionally beneficial to amplify some or all of the nucleic acids in the sample. In some embodiments, the nucleic acids are amplified using polymerase chain reactions (PCR) techniques known in the art.

One example of a sequencing technology that can be used in the methods of the provided invention is Illumina sequencing (e.g., the MiSeq™ platform), which is a polymerase-based sequence-by-synthesis that may be utilized to amplify DNA or RNA. Illumina sequencing for DNA is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. When using Illumina sequencing to detect RNA the same method applies except RNA fragments are being isolated and amplified in order to determine the RNA expression of the sample. After the sequences are interrogated with the sequencer, they may be output in a data file, such as a FASTQ file, which is a text-based format for storing biological sequence and quality scores (see discussion above).

Another example of a DNA sequencing technique that may be used in the methods of the provided invention is Ion Torrent™ sequencing, offered by Life Technologies. See U.S. patent application numbers 2009/0026082, 2009/0127589, 2010/0035252, 2010/0137143, 2010/0188073, 2010/0197507, 2010/0282617, 2010/0300559, 2010/0300895, 2010/0301398, and 2010/0304982, the content of each of which is incorporated by reference herein in its entirety. In Ion Torrent™ sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and is attached at a resolution such that the fragments are individually resolvable. Addition of one or more nucleotides releases a proton (H+), which signal detected and recorded in a sequencing instrument. The signal strength is proportional to the number of nucleotides incorporated. Ion Torrent data may also be output as a FASTQ file.

Another example of a DNA and RNA sequencing technique that can be used in the methods of the provided invention is 454™ sequencing (Roche) (Margulies, M et al. 2005, Nature, 437, 376-380). 454™ sequencing is a sequencing-by-synthesis technology that utilizes also utilizes pyrosequencing. 454™ sequencing of DNA involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed. In another embodiment, pyrosequencing is used to measure gene expression. Pyrosequencing of RNA applies similar to pyrosequencing of DNA, and is accomplished by attaching applications of partial rRNA gene sequencings to microscopic beads and then placing the attachments into individual wells. The attached partial rRNA sequence are then amplified in order to determine the gene expression profile. Sharon Marsh, *Pyrosequencing® Protocols in Methods in Molecular Biology*, Vol. 373, 15-23 (2007).

Another example of a DNA and RNA detection techniques that may be used in the methods of the provided invention is SOLiD™ technology (Applied Biosystems). SOLiD™ technology systems is a ligation based sequencing technology that may utilized to run massively parallel next generation sequencing of both DNA and RNA. In DNA SOLiD™ sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In other embodiments, SOLiD™ Serial Analysis of Gene Expression (SAGE) is used to measure gene expression. Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., Science 270:484 487 (1995); and Velculescu et al., Cell 88:243 51 (1997, the contents of each of which are incorporated by reference herein in their entirety).

Another sequencing technique that can be used in the methods of the provided invention includes, for example, Helicos True Single Molecule Sequencing (tSMS) (Harris T. D. et al. (2008) Science 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step. Further description of tSMS is shown for example in Lapidus et al. (U.S. Pat. No. 7,169,560), Lapidus et al. (U.S. patent application No. 2009/0191565), Quake et al. (U.S. Pat. No. 6,818,395), Harris (U.S. Pat. No. 7,282, 337), Quake et al. (U.S. patent application No. 2002/0164629), and Braslaysky, et al., PNAS (USA), 100: 3960-3964 (2003), the contents of each of these references is incorporated by reference herein in its entirety.

Another example of a sequencing technology that may be used in the methods of the provided invention includes the single molecule, real-time (SMRT) technology of Pacific Biosciences to sequence both DNA and RNA. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated. In order to sequence RNA, the DNA polymerase is replaced with a with a reverse transcriptase in the ZMW, and the process is followed accordingly.

Another example of a sequencing technique that can be used in the methods of the provided invention is nanopore sequencing (Soni G V and Meller, AClin Chem 53: 1996-2001) (2007). A nanopore is a small hole, of the order of I nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using a chemical-sensitive field effect transistor (chemFET) array to sequence DNA (for example, as described in US Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used in the methods of the provided invention involves using an electron microscope (Moudrianakis E. N. and Beer M. Proc Natl Acad Sci USA. 1965 March; 53:564-71). In one example of the technique, individual DNA molecules are labeled using metallic labels that are distinguishable using an electron microscope. These molecules are then stretched on a flat surface and imaged using an electron microscope to measure sequences.

Additional detection methods can utilize binding to microarrays for subsequent fluorescent or non-fluorescent detection, barcode mass detection using a mass spectrometric methods, detection of emitted radiowaves, detection of scattered light from aligned barcodes, fluorescence detection using quantitative PCR or digital PCR methods. A comparative nucleic acid hybridization array is a technique for detecting copy number variations within the patient's sample DNA. The sample DNA and a reference DNA are differently labeled using distinct fluorophores, for example, and then hybridized to numerous probes. The fluorescent intensity of the sample and reference is then measured, and the fluorescent intensity ratio is then used to calculate copy number variations. Methods of comparative genomic hybridization array are discussed in more detail in Shinawi M, Cheung S W *The array CGH and its clinical applications*, Drug Discovery Today 13 (17-18): 760-70. Microarray detection may not produce a FASTQ file directly, however programs are available to convert the data produced by the microarray sequencers to a FASTQ, or similar, format.

Another method of detecting DNA molecules, RNA molecules, and copy number is fluorescent in situ hybridization (FISH). In Situ Hybridization Protocols (Ian Darby ed., 2000). FISH is a molecular cytogenetic technique that detects specific chromosomal rearrangements such as mutations in a DNA sequence and copy number variances. A DNA molecule is chemically denatured and separated into two strands. A single stranded probe is then incubated with a denatured strand of the DNA. The signals stranded probe is selected depending target sequence portion and has a high affinity to the complementary sequence portion. Probes may include a repetitive sequence probe, a whole chromosome probe, and locus-specific probes. While incubating, the combined probe and DNA strand are hybridized. The results are then visualized and quantified under a microscope in order to assess any variations.

In another embodiment, a MassARRAY™-based gene expression profiling method is used to measure gene expression. In the MassARRAY™-based gene expression profiling method, developed by Sequenom, Inc. (San Diego, Calif.) following the isolation of RNA and reverse transcription, the obtained cDNA is spiked with a synthetic DNA molecule (competitor), which matches the targeted cDNA region in all positions, except a single base, and serves as an internal standard. The cDNA/competitor mixture is PCR amplified and is subjected to a post-PCR shrimp alkaline phosphatase (SAP) enzyme treatment, which results in the dephosphorylation of the remaining nucleotides. After inactivation of the alkaline phosphatase, the PCR products from the competitor and cDNA are subjected to primer extension, which generates distinct mass signals for the competitor- and cDNA-derives PCR products. After purification, these products are dispensed on a chip array, which is pre-loaded with components needed for analysis with matrix-assisted laser desorption ionization time-of-flight mass spectrometry (MALDI-TOF MS) analysis. The cDNA present in the reaction is then quantified by analyzing the ratios of the peak areas in the mass spectrum generated. For further details see, e.g., Ding and Cantor, Proc. Natl. Acad. Sci. USA 100:3059 3064 (2003).

Further PCR-based techniques include, for example, differential display (Liang and Pardee, Science 257:967 971 (1992)); amplified fragment length polymorphism (iAFLP) (Kawamoto et al., Genome Res. 12:1305 1312 (1999)); BeadArray™ technology (Illumina, San Diego, Calif.; Oliphant et al., Discovery of Markers for Disease (Supplement to Biotechniques), June 2002; Ferguson et al., Analytical Chemistry 72:5618 (2000)); Beads Array for Detection of Gene Expression (BADGE), using the commercially available Luminex100 LabMAP system and multiple color-coded microspheres (Luminex Corp., Austin, Tex.) in a rapid assay for gene expression (Yang et al., Genome Res. 11:1888 1898 (2001)); and high coverage expression profiling (HiCEP) analysis (Fukumura et al., Nucl. Acids. Res. 31(16) e94 (2003)). The contents of each of which are incorporated by reference herein in their entirety.

In certain embodiments, variances in gene expression can also be identified, or confirmed using a microarray techniques, including nylon membrane arrays, microchip arrays and glass slide arrays, e.g., such as available commercially from Affymetrix (Santa Clara, Calif.). Generally, RNA samples are isolated and converted into labeled cDNA via reverse transcription. The labeled cDNA is then hybridized onto either a nylon membrane, microchip, or a glass slide with specific DNA probes from cells or tissues of interest. The hybridized cDNA is then detected and quantified, and the resulting gene expression data may be compared to controls for analysis. The methods of labeling, hybridization, and detection vary depending on whether the microarray support is a nylon membrane, microchip, or glass slide. Nylon membrane arrays are typically hybridized with P-dNTP labeled probes. Glass slide arrays typically involve labeling with two distinct fluorescently labeled nucleotides. Methods for making microarrays and determining gene product expression (e.g., RNA or protein) are shown in Yeatman et al. (U.S. patent application No. 2006/0195269), the content of which is incorporated by reference herein in its entirety.

In some embodiments, mass spectrometry (MS) analysis can be used alone or in combination with other methods (e.g., immunoassays or RNA measuring assays) to determine the presence and/or quantity of the one or more biomarkers disclosed herein in a biological sample. In some embodiments, the MS analysis includes matrix-assisted laser desorption/ionization (MALDI time-of-flight (TOF) MS analysis, such as for example direct-spot MALDI-TOF or liquid chromatography MALDI-TOF mass spectrometry analysis. In some embodiments, the MS analysis comprises electrospray ionization (ESI) MS, such as for example liquid chromatography (LC) ESI-MS. Mass analysis can be accomplished using commercially-available spectrometers. Methods for utilizing MS analysis, including MALDI-TOF MS and ESI-MS, to detect the presence and quantity of biomarker peptides in biological samples are known in the art. See for example U.S. Pat. Nos. 6,925,389; 6,989,100; and 6,890,763 for further guidance, each of which is incorporated by reference herein in their entirety.

Protein sequences for use with the methods, sequence constructs, and systems of the invention can be determined using a number of techniques known to those skilled in the relevant art. For example, amino acid sequences and amino acid sequence reads may be produced by analyzing a protein or a portion of a protein with mass spectrometry or using Edman degradation. Mass spectrometry may include, for example, matrix-assisted laser desorption/ionization (MALDI) time-of-flight (TOF) MS analysis, such as for example direct-spot MALDI-TOF or liquid chromatography MALDI-TOF mass spectrometry analysis, electrospray ionization (ESI) MS, such as for example liquid chromatography (LC) ESI-MS, or other techniques such as MS-MS. Edman degradation analysis may be performed using commercial instruments such as the Model 49x Procise protein/peptide sequencer (Applied Biosystems/Life Technologies). The sequenced amino acid sequences, i.e., polypeptides, i.e., proteins, may be at least 10 amino acids in length, e.g., at least 20 amino acids in length, e.g., at least 50 amino acids in length.

Incorporation by Reference

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A system for identifying cancer-induced genetic mutations, the system comprising:
   at least one computer hardware processor; and
   at least one non-transitory computer-readable storage medium storing processor-executable instructions that, when executed by the at least one computer hardware processor, cause the at least one computer hardware processor to perform:
   aligning a first plurality of sequence reads from a non-cancerous sample from a subject to a reference sequence;
   representing, in the at least one non-transitory computer-readable storage medium, one or more differences between the first plurality of sequence reads and the reference sequence as two or more alternative paths in a first graph data structure comprising nodes and edges, wherein each alternative path is placed at a position in the first graph data structure where there is a difference between at least one sequence read and the reference sequence;
   aligning a second plurality of sequence reads from a cancerous sample from the subject to the first graph data structure, wherein the aligning considers two or more alternative paths by looking backwards to any prior paths on the first graph data structure to find a maximum score; and identifying one or more differences between the second plurality of sequence reads and the first graph data structure as new mutations correlated with the cancer.

2. The system of claim 1, wherein the reference sequence comprises a graph data structure.

3. The system of claim 1, wherein the first graph data structure is a directed acyclic graph (DAG).

4. The system of claim 1, wherein each node in the first graph data structure stores one or more nucleotide symbols.

5. The system of claim 4, wherein each alternative path is created by breaking the reference sequence into nodes before and after the difference, and creating a path between the nodes that represents the reference sequence and another path between the nodes representing the difference, thereby creating the first graph data structure against which nucleic acid reads can be aligned.

6. The system of claim 1, wherein the instructions further comprise:
preparing a second graph data structure representing the differences between the first plurality of sequence reads, the second plurality of sequence reads, and the reference sequence;
aligning a third plurality of sequence reads from an advanced cancerous sample from the subject to the second graph data structure; and
identifying one or more differences between the third plurality of sequence reads and the second graph data structure as new mutations correlated with the advanced cancerous sample.

7. The system of claim 6, wherein the second plurality of sequence reads represents a major genetic clone due to the cancer.

8. The system of claim 6, wherein the third plurality of sequence reads represent a minor genetic clone due to the cancer.

9. The system of claim 1, wherein the instructions further comprise representing the new mutations correlated with the cancer as alternative paths in the first graph data structure.

10. The system of claim 1, wherein the instructions further comprise aligning one or more sequence reads from a third plurality of sequence reads corresponding to a sample later collected from the subject to the first graph data structure, and monitoring cancer progression or recurrence based on the alignment.

11. The system of claim 1, wherein the instructions further comprise reporting the new mutations correlated with the cancer to a health care provider.

12. The system of claim 1, wherein the instructions comprise diagnosing the subject as having an advanced stage of the cancer based on the identified one or more differences between the second plurality of sequence reads and the first graph data structure.

13. The system of claim 1, wherein the reference sequence is the human genome.

14. A method of identifying cancer-induced genetic mutations, comprising using a processor coupled to a non-transitory computer-readable storage medium to perform:
aligning a first plurality of sequence reads from a non-cancerous sample from a subject to a reference sequence;
representing, in the non-transitory computer-readable storage medium, one or more differences between the first plurality of sequence reads and the reference sequence as two or more alternative paths in a first graph data structure comprising nodes and edges, wherein each alternative path is placed at a position in the first graph data structure where there is a difference between at least one sequence read and the reference sequence;
aligning a second plurality of sequence reads from a cancerous sample from the subject to the first graph data structure, wherein the aligning considers two or more alternative paths by looking backwards to any prior paths on the first graph data structure to find a maximum score; and
identifying one or more differences between the second plurality of sequence reads and the first graph data structure as new mutations correlated with the cancer.

15. The method of claim 14, wherein each alternative path is created by breaking the reference sequence into nodes before and after the difference, and creating a path between the nodes that represents the reference sequence and another path between the nodes representing the difference, thereby creating the first graph data structure against which nucleic acid reads can be aligned.

16. The method of claim 14, further comprising:
preparing a second graph data structure representing the differences between the first plurality of sequence reads, the second plurality of sequence reads, and the reference sequence;
aligning a third plurality of sequence reads from an advanced cancerous sample from the subject to the second graph data structure; and
identifying one or more differences between the third plurality of sequence reads and the second graph data structure as new mutations correlated with the advanced cancerous sample.

17. The method of claim 14, further comprising:
aligning one or more sequence reads from a third plurality of sequence reads corresponding to a sample later collected from the subject to the first graph data structure; and monitoring cancer progression or recurrence based on the alignment.

18. The method of claim 14, further comprising diagnosing the subject as having an advanced stage of the cancer based on the identified one or more differences between the second plurality of sequence reads and the first graph data structure.

19. The method of claim 14, wherein the reference sequence is the human genome.

20. At least one non-transitory computer-readable storage medium storing processor-executable instructions that, when executed by at least one computer hardware processor, cause the at least one computer hardware processor to perform:
aligning a first plurality of sequence reads from a non-cancerous sample from a subject to a reference sequence;
representing, in the non-transitory computer-readable storage medium, one or more differences between the first plurality of sequence reads and the reference sequence as two or more alternative paths in a first graph data structure comprising nodes and edges, wherein each alternative path is placed at a position in the first graph data structure where there is a difference between at least one sequence read and the reference sequence;
aligning a second plurality of sequence reads from a cancerous sample from the subject to the first graph data structure, wherein the aligning considers two or more alternative paths by looking backwards to any prior paths on the first graph data structure to find a maximum score; and identifying one or more differences between the second plurality of sequence reads and the first graph data structure as new mutations correlated with the cancer.

\* \* \* \* \*